(12) United States Patent
Gartstein et al.

(10) Patent No.: US 9,376,648 B2
(45) Date of Patent: Jun. 28, 2016

(54) FOAM MANIPULATION COMPOSITIONS CONTAINING FINE PARTICLES

(75) Inventors: Vladimir Gartstein, Mason, OH (US);
Faiz F. Sherman, Mason, OH (US);
Hiroshi Oh, Cincinnati, OH (US);
Robert Lupitskyy, Potsdam, NY (US);
Mikhail Motornov, Potsdam, NY (US);
Sergiy Minko, Potsdam, NY (US)

(73) Assignee: The Procter & Gamble Company, Cincinnati, OH (US)

( * ) Notice: Subject to any disclaimer, the term of this patent is extended or adjusted under 35 U.S.C. 154(b) by 803 days.

(21) Appl. No.: 12/098,749

(22) Filed: Apr. 7, 2008

(65) Prior Publication Data
US 2009/0252691 A1    Oct. 8, 2009

(51) Int. Cl.
| | |
|---|---|
| *A61K 8/11* | (2006.01) |
| *A61Q 19/00* | (2006.01) |
| *C11D 3/00* | (2006.01) |
| *A61K 8/25* | (2006.01) |
| *A61K 8/26* | (2006.01) |
| *A61K 8/46* | (2006.01) |
| *A61K 8/891* | (2006.01) |
| *C11D 3/12* | (2006.01) |

(52) U.S. Cl.
CPC .............. *C11D 3/0026* (2013.01); *A61K 8/11* (2013.01); *A61K 8/25* (2013.01); *A61K 8/26* (2013.01); *A61K 8/466* (2013.01); *A61K 8/891* (2013.01); *A61Q 19/00* (2013.01); *C11D 3/1213* (2013.01); *C11D 3/1246* (2013.01); *A61K 2800/412* (2013.01); *Y10S 977/773* (2013.01)

(58) Field of Classification Search
CPC .................................................... C11D 3/0026
See application file for complete search history.

(56) References Cited

U.S. PATENT DOCUMENTS

| | | |
|---|---|---|
| 2,220,099 A | 11/1940 | Heidelberg et al. |
| 2,472,590 A | 6/1949 | Kenyon |
| 2,477,383 A | 7/1949 | Lewis |
| 3,377,339 A | 4/1968 | Sisido |

(Continued)

FOREIGN PATENT DOCUMENTS

| | | |
|---|---|---|
| EP | 0054325 B1 | 4/1984 |
| EP | 0145438 A2 | 6/1985 |

(Continued)

OTHER PUBLICATIONS

KG Marinova, ND Denkov, P Branlard, Y Giraud, M Deruelle. "Optimal Hydrophobicity of Silica in Mixed Oil-Silica Antifoams." Langmuir. vol. 18 No. 9, Apr. 30, 2002, pp. 3399-3403.*

(Continued)

*Primary Examiner* — Isaac Shomer
(74) *Attorney, Agent, or Firm* — Jason J Camp

(57) ABSTRACT

A foam manipulation stabilizing composition for use in consumer products includes a plurality of surface-modified particles in combination with at least one surfactant. The particles have an average particle size greater than 100 nm up to about 50 μm and a hydrophobicity measured by a contact angle between about 20° to 140°. The ratio of particles-to-surfactant may be between about 1:20 to about 20:1. The surface modification may include grafting pH or temperature switching functional groups to the particles or to a composition, such as a polymer, coated on the particle. A method for reducing the level of foam in a rinse solution is also described.

18 Claims, 16 Drawing Sheets

(56) References Cited

U.S. PATENT DOCUMENTS

| | | |
|---|---|---|
| 3,902,940 A | 9/1975 | Heller, Jr. et al. |
| 3,929,678 A | 12/1975 | Laughlin et al. |
| 4,228,042 A | 10/1980 | Letton |
| 4,239,660 A | 12/1980 | Kingry |
| 4,260,529 A | 4/1981 | Letton |
| 4,274,977 A * | 6/1981 | Koerner et al. ............... 516/117 |
| 4,443,357 A | 4/1984 | Maloney et al. |
| 4,511,497 A | 4/1985 | Ehrlich |
| 4,532,067 A | 7/1985 | Padron |
| 4,545,919 A | 10/1985 | Abel |
| 4,576,744 A | 3/1986 | Edwards |
| 4,597,898 A | 7/1986 | Vander Meer |
| 4,637,891 A | 1/1987 | Delwel et al. |
| 4,661,288 A | 4/1987 | Rubingh |
| 4,702,857 A | 10/1987 | Gosselink |
| 4,711,730 A | 12/1987 | Gosselink |
| 4,713,194 A | 12/1987 | Gosselink |
| 4,716,186 A | 12/1987 | Portnoy |
| 4,720,544 A | 1/1988 | Schouten |
| 4,721,580 A | 1/1988 | Gosselink |
| 4,726,908 A | 2/1988 | Kruse et al. |
| 4,816,188 A | 3/1989 | Kitano et al. |
| 4,841,040 A | 6/1989 | Just |
| 4,861,512 A | 8/1989 | Gosselink |
| 4,877,896 A | 10/1989 | Maldonado |
| 4,976,879 A | 12/1990 | Maldonado |
| 5,009,882 A | 4/1991 | Degenhardt |
| 5,096,617 A * | 3/1992 | Ball et al. ............... 516/116 |
| 5,133,924 A | 7/1992 | Appel et al. |
| 5,152,932 A | 10/1992 | Mueller |
| 5,160,657 A | 11/1992 | Bortolotti et al. |
| 5,164,108 A | 11/1992 | Appel et al. |
| 5,182,043 A | 1/1993 | Morrall |
| 5,256,168 A | 10/1993 | Morrall |
| 5,259,984 A | 11/1993 | Hull |
| 5,318,728 A | 6/1994 | Surutzidis |
| 5,329,030 A | 7/1994 | Schenker et al. |
| 5,369,135 A | 11/1994 | Campbell et al. |
| 5,382,677 A | 1/1995 | Colignon et al. |
| 5,387,617 A | 2/1995 | Hedstrand et al. |
| 5,412,118 A | 5/1995 | Vermeer |
| 5,415,807 A | 5/1995 | Gosselink |
| 5,437,810 A | 8/1995 | Ewbank |
| 5,475,134 A | 12/1995 | Baker |
| 5,541,316 A | 7/1996 | Engelskirchen |
| 5,560,748 A * | 10/1996 | Surutzidis et al. ............... 8/111 |
| 5,565,556 A | 10/1996 | Heinzman |
| 5,569,645 A | 10/1996 | Dinniwell et al. |
| 5,587,500 A | 12/1996 | Hovda |
| 5,599,782 A | 2/1997 | Pan |
| 5,599,977 A | 2/1997 | Kiely |
| 5,691,298 A | 11/1997 | Gosselink |
| 5,723,434 A | 3/1998 | Falk |
| 5,756,447 A | 5/1998 | Hall |
| 5,767,053 A | 6/1998 | Germain et al. |
| 5,773,401 A | 6/1998 | Murata |
| 5,776,878 A | 7/1998 | Thoen |
| 5,821,360 A | 10/1998 | Engelskirchen |
| 5,830,839 A * | 11/1998 | Scepanski ............... 510/305 |
| 5,837,666 A | 11/1998 | Murata |
| 5,843,878 A | 12/1998 | Gosselink |
| 5,851,235 A | 12/1998 | Baillely |
| 5,856,470 A | 1/1999 | Moeller |
| 5,892,027 A | 4/1999 | Moeller |
| 5,932,532 A | 8/1999 | Ghosh |
| 5,959,101 A | 9/1999 | Engelskirchen |
| 5,985,813 A | 11/1999 | Arvanitidou |
| 6,004,918 A | 12/1999 | Adams |
| 6,004,922 A | 12/1999 | Watson et al. |
| 6,008,181 A | 12/1999 | Cripe et al. |
| 6,018,033 A | 1/2000 | Chen et al. |
| 6,020,295 A | 2/2000 | Harrison |
| 6,020,303 A | 2/2000 | Cripe et al. |
| 6,022,844 A | 2/2000 | Baillely et al. |
| 6,060,443 A | 5/2000 | Cripe et al. |
| 6,111,097 A | 8/2000 | Nagashima |
| 6,136,769 A | 10/2000 | Asano et al. |
| 6,207,771 B1 | 3/2001 | Larson |
| 6,221,826 B1 | 4/2001 | Surutzidis |
| 6,271,278 B1 | 8/2001 | Park |
| 6,274,540 B1 | 8/2001 | Scheibel et al. |
| 6,314,926 B1 | 11/2001 | Meneely et al. |
| 6,331,619 B1 | 12/2001 | Besemer |
| 6,353,037 B1 | 3/2002 | Thunhorst et al. |
| 6,444,633 B2 | 9/2002 | Price |
| 6,452,035 B2 | 9/2002 | Dupont |
| 6,472,358 B1 | 10/2002 | Richter |
| 6,498,269 B1 | 12/2002 | Merbouh |
| 6,518,337 B1 | 2/2003 | Baker |
| 6,566,319 B1 | 5/2003 | Scheibel et al. |
| 6,583,096 B1 | 6/2003 | Kott et al. |
| 6,586,483 B2 | 7/2003 | Kolb et al. |
| 6,596,680 B2 | 7/2003 | Kott et al. |
| 6,602,840 B1 | 8/2003 | Scheibel et al. |
| 6,605,351 B1 | 8/2003 | Rossmy et al. |
| 6,608,229 B2 | 8/2003 | Bragd |
| 6,613,733 B1 | 9/2003 | Barnabas |
| 6,617,447 B2 | 9/2003 | Gnad |
| 6,635,755 B1 | 10/2003 | Jaschinski |
| 6,673,961 B2 | 1/2004 | Connor et al. |
| 6,677,289 B1 | 1/2004 | Price |
| 6,774,096 B1 | 8/2004 | Paye |
| 6,777,548 B1 | 8/2004 | Kesselmans |
| 6,780,830 B1 | 8/2004 | Huish et al. |
| 6,790,822 B1 | 9/2004 | Baba |
| 6,818,163 B1 | 11/2004 | Fibiger et al. |
| 6,822,091 B1 | 11/2004 | Kesselmans |
| 6,866,888 B2 | 3/2005 | Baker |
| 6,874,518 B2 | 4/2005 | Porter |
| 6,893,497 B2 | 5/2005 | Einfeldt |
| 6,894,012 B2 * | 5/2005 | Sebillotte-Arnaud et al. ............... 510/136 |
| 6,908,894 B2 | 6/2005 | Kott et al. |
| 6,933,269 B2 | 8/2005 | Jordan |
| 6,936,710 B2 | 8/2005 | Bragd |
| 7,033,975 B2 | 4/2006 | Baran, Jr. et al. |
| 7,141,612 B2 | 11/2006 | Baran, Jr. et al. |
| 7,217,752 B2 | 5/2007 | Schmucker-Castner et al. |
| 7,326,675 B2 | 2/2008 | Schneiderman |
| 7,332,467 B2 | 2/2008 | Schneiderman |
| 7,358,220 B2 | 4/2008 | Scheibel |
| 7,695,814 B2 * | 4/2010 | Gartstein ............... A61K 8/11 428/407 |
| 2002/0123447 A1 | 9/2002 | Manske |
| 2002/0128336 A1 * | 9/2002 | Kolb et al. ............... 521/50 |
| 2002/0143172 A1 | 10/2002 | Ookawa |
| 2002/0160928 A1 * | 10/2002 | Smerznak ............... C11D 1/72 510/405 |
| 2003/0012757 A1 * | 1/2003 | Barbuzzi ............... A61K 8/0241 424/70.1 |
| 2003/0051726 A1 | 3/2003 | Leininger |
| 2003/0134420 A1 * | 7/2003 | Lollo et al. ............... 435/455 |
| 2003/0134761 A1 * | 7/2003 | Sebillotte-Arnaud et al. ............... 510/130 |
| 2004/0039191 A1 | 2/2004 | Volkert |
| 2004/0106502 A1 | 6/2004 | Sher |
| 2005/0026803 A1 | 2/2005 | Sivik |
| 2005/0070703 A1 | 3/2005 | Muller et al. |
| 2005/0106686 A1 | 5/2005 | Jetten |
| 2005/0112356 A1 | 5/2005 | Rynd et al. |
| 2005/0121159 A1 | 6/2005 | Jetten |
| 2005/0153860 A1 | 7/2005 | Zhou |
| 2005/0153867 A1 | 7/2005 | Scheibel |
| 2005/0155936 A1 | 7/2005 | Martin |
| 2005/0187133 A1 | 8/2005 | Schneiderman |
| 2005/0209476 A1 | 9/2005 | Reilman |
| 2005/0239675 A1 | 10/2005 | Makansi |
| 2005/0249778 A1 | 11/2005 | Narayan |
| 2006/0030513 A1 | 2/2006 | Binder |
| 2006/0074184 A1 | 4/2006 | Guillet et al. |
| 2006/0100292 A1 | 5/2006 | Nolan et al. |
| 2006/0135391 A1 | 6/2006 | Scheibel |
| 2006/0135636 A1 | 6/2006 | Zhu et al. |
| 2006/0189506 A1 | 8/2006 | Muller |

(56) References Cited

U.S. PATENT DOCUMENTS

| | | |
|---|---|---|
| 2006/0204528 A1 | 9/2006 | Nolte et al. |
| 2006/0264523 A1 | 11/2006 | Lee et al. |
| 2007/0099815 A1 | 5/2007 | Song |
| 2007/0105742 A1 | 5/2007 | Scheibel |
| 2007/0190327 A1* | 8/2007 | Gartstein ............ A61K 8/11 428/405 |

FOREIGN PATENT DOCUMENTS

| | | |
|---|---|---|
| EP | 0146395 A2 | 6/1985 |
| EP | 0157553 A2 | 10/1985 |
| EP | 0256696 A1 | 2/1988 |
| EP | 0362916 A2 | 4/1990 |
| EP | 0164554 B1 | 10/1991 |
| EP | 0462042 A1 | 12/1991 |
| EP | 0472042 A1 | 2/1992 |
| EP | 0579664 B1 | 1/1994 |
| EP | 0639638 A1 | 2/1995 |
| EP | 0425369 B1 | 11/1995 |
| EP | 0455522 B1 | 8/1996 |
| EP | 0755944 A2 | 1/1997 |
| EP | 0769548 A | 4/1997 |
| EP | 0601403 B1 | 10/1997 |
| EP | 0815879 A2 | 1/1998 |
| EP | 0874889 A1 | 11/1998 |
| EP | 0892041 A1 | 1/1999 |
| EP | 0511081 B1 | 6/1999 |
| EP | 0920874 A1 | 6/1999 |
| EP | 0885245 B1 | 11/1999 |
| EP | 0907664 B1 | 8/2000 |
| EP | 1038945 A2 | 9/2000 |
| EP | 0904298 B1 | 4/2002 |
| EP | 1251140 A1 | 10/2002 |
| EP | 1371718 A1 | 12/2003 |
| EP | 1487507 B1 | 12/2004 |
| EP | 1529820 A1 | 5/2005 |
| EP | 1566390 A1 | 8/2005 |
| GB | 2272449 A | 5/1994 |
| GB | 2283754 A | 5/1995 |
| JP | 56081358 A | 7/1981 |
| JP | 57130545 A | 8/1982 |
| JP | 61040301 A | 2/1986 |
| JP | 61152702 A | 7/1986 |
| JP | 62058954 A | 3/1987 |
| JP | 63154611 A | 6/1988 |
| JP | 06279504 A | 10/1994 |
| JP | 07172893 A2 | 7/1995 |
| JP | 10183175 A | 12/1996 |
| JP | 09052901 A2 | 2/1997 |
| JP | 09316103 A | 12/1997 |
| JP | 10025144 A2 | 1/1998 |
| JP | 10072501 A2 | 3/1998 |
| JP | 10167772 A2 | 7/1998 |
| JP | 10183174 A | 7/1998 |
| JP | 10195101 A | 7/1998 |
| JP | 10195102 A | 7/1998 |
| JP | 10195488 A | 7/1998 |
| JP | 10279991 A | 10/1998 |
| JP | 10279602 A | 10/1998 |
| JP | 10298203 A2 | 11/1998 |
| JP | 11012301 A2 | 1/1999 |
| JP | 11012302 A2 | 1/1999 |
| JP | 11029601 A2 | 2/1999 |
| JP | 11060602 A | 3/1999 |
| JP | 11140101 A | 5/1999 |
| JP | 11310601 A | 11/1999 |
| JP | 11322804 A | 11/1999 |
| JP | 11322805 A | 11/1999 |
| JP | 2000001503 A | 1/2000 |
| JP | 2000007704 A | 1/2000 |
| JP | 2000159803 A | 6/2000 |
| JP | 2000159804 A | 6/2000 |
| JP | 2000159805 A | 6/2000 |
| JP | 2000178301 A | 6/2000 |
| JP | 2001049591 A | 2/2001 |
| JP | 2001089502 A | 4/2001 |
| JP | 2003180812 A | 7/2003 |
| JP | 2003183302 A | 7/2003 |
| JP | 2005162969 A | 6/2005 |
| WO | WO8910940 A1 | 11/1989 |
| WO | WO-9112312 A | 8/1991 |
| WO | WO9113138 A1 | 9/1991 |
| WO | WO-9423009 A | 10/1994 |
| WO | WO9502614 A1 | 1/1995 |
| WO | WO 95/05444 A1 | 2/1995 |
| WO | WO9507303 A1 | 3/1995 |
| WO | WO9532272 A1 | 11/1995 |
| WO | WO9533032 A1 | 12/1995 |
| WO | WO9533814 A1 | 12/1995 |
| WO | WO9600771 A1 | 1/1996 |
| WO | WO9603439 A1 | 2/1996 |
| WO | WO9637595 A1 | 11/1996 |
| WO | WO9716514 A1 | 5/1997 |
| WO | WO9732902 A1 | 9/1997 |
| WO | WO9732903 A1 | 9/1997 |
| WO | WO9742282 A1 | 11/1997 |
| WO | WO9742284 A1 | 11/1997 |
| WO | WO9742285 A1 | 11/1997 |
| WO | WO9742286 A1 | 11/1997 |
| WO | WO9742288 A1 | 11/1997 |
| WO | WO9742292 A1 | 11/1997 |
| WO | WO9742293 A1 | 11/1997 |
| WO | WO9743367 A1 | 11/1997 |
| WO | WO9745510 A1 | 12/1997 |
| WO | WO9808925 A1 | 3/1998 |
| WO | WO9808928 A1 | 3/1998 |
| WO | WO9817755 A1 | 4/1998 |
| WO | WO 98/18434 A1 | 5/1998 |
| WO | WO9835002 | 8/1998 |
| WO | WO9835003 A1 | 8/1998 |
| WO | WO9835004 | 8/1998 |
| WO | WO9835005 A1 | 8/1998 |
| WO | WO9835006 A1 | 8/1998 |
| WO | WO9901530 A1 | 1/1999 |
| WO | WO9905084 A1 | 2/1999 |
| WO | WO9923240 A1 | 5/1999 |
| WO | WO9931211 A1 | 6/1999 |
| WO | WO9949009 A1 | 9/1999 |
| WO | WO9967353 A1 | 12/1999 |
| WO | WO0037598 A1 | 6/2000 |
| WO | WO0061639 A1 | 10/2000 |
| WO | WO0071240 A1 | 11/2000 |
| WO | WO0071241 A1 | 11/2000 |
| WO | WO0105874 A1 | 1/2001 |
| WO | WO0105923 A1 | 1/2001 |
| WO | WO0129112 A1 | 4/2001 |
| WO | WO0148058 A1 | 7/2001 |
| WO | WO0162884 A1 | 8/2001 |
| WO | WO0188075 A1 | 11/2001 |
| WO | WO0192451 A1 | 12/2001 |
| WO | WO0222772 A1 | 3/2002 |
| WO | WO03010206 A1 | 2/2003 |
| WO | WO03010267 A1 | 2/2003 |
| WO | WO03040279 A1 | 5/2003 |
| WO | WO2004024858 A1 | 3/2004 |
| WO | WO2004065425 A1 | 8/2004 |
| WO | WO2004069972 A1 | 8/2004 |
| WO | WO2004069973 A1 | 8/2004 |
| WO | WO2004069974 A2 | 8/2004 |
| WO | WO2004069975 A1 | 8/2004 |
| WO | WO2004069976 A2 | 8/2004 |
| WO | WO2004069977 A1 | 8/2004 |
| WO | WO2004069978 A1 | 8/2004 |
| WO | WO2004091557 A2 | 10/2004 |
| WO | WO2005059152 A1 | 6/2005 |
| WO | WO2005063957 A2 | 7/2005 |
| WO | WO 2006/033981 A1 | 3/2006 |
| WO | WO 2006/034857 A2 | 4/2006 |
| WO | WO 2006/042176 A1 | 4/2006 |
| WO | WO2006113314 A1 | 10/2006 |
| WO | WO2006113315 A2 | 10/2006 |

(56) References Cited

FOREIGN PATENT DOCUMENTS

| WO | WO 2007/068344 A1 | 6/2007 |
| WO | WO2007149806 A1 | 12/2007 |
| WO | WO2008007320 A2 | 1/2008 |

OTHER PUBLICATIONS

DA Edwards, J Hanes, G Caponetti, J Hrkach, A Ben-Jebria, ML Eskew, J Mintzes, D Deaver, N Lotan, R Langer. Large Porous Particles for Pulmonary Drug Delivery. Science, vol. 276, Jun. 20, 1997, pp. 1868-1871.*

ND Denkov. "Mechanisms of Foam Destruction by Oil-Based Antifoams." Langmuir, vol. 20, 2004, pp. 9463-9505.*

B Binks, TS Horozov. "Aqueous Foams Stabilized Solely by Silica Nanoparticles." Angew Chem, vol. 117, 2-5, pp. 3788-3791.*

B Arkles. "Hydrophobicity, Hydrophilicity and Silanes." Paint & Coatings Industry, Oct. 2006, 10 pages.*

LT Zhuravlev. "The surface chemistry of amorphous silica. Zhuravlev model." Colloids and Surfaces A: Physiochemical and Engineering Aspects. vol. 173, 2000, pp. 1-38.*

L Bergman, J Rosenholm, AB Ost, A Duchanoy, P Kankaanpaa, J Heino, M Linden. "On the Complexity of Electrostatic Suspension Stabilization of Functionalized Silica Nanoparticles for Biotargeting and Imaging Applications." Journal of Nanomaterials, vol. 2008, Article ID 712514, 9 pages.*

L Bergman, J Rosenholm, AB Ost, A Duchanoy, P Kankaanpaa, J Heino, M Linden. Abstract for article in the Journal of Nanometerials. http://connection.ebscohost.com/c/articles/36264870/complexity-electrostatic-suspension-stabilization-functionalized-silica-nanoparticles-biotargeting-imaging-applications, accessed May 7, 2015, 2 printed pages.*

BP Binks, R Murakami, SP Armes, S Fujii, A Schmid. "pH-Responsive Aqueous Foams Stabilized by Ionizable Latex Particles." Langmuir, vol. 23, 2007, pp. 8691-8694, published on web Jul. 21, 2007.*

Kim, Jin-Woong et al., "Synthesis of Nonspherical Colloidal Particles with Anisotropic Properties," J. Am. Chem. Soc., 128 (44), pp. 14374-14377 (2006).

Stöber, W. et al., "Controlled Growth of Monodisperse Silica Spheres in the Micron Size Range," Journal of Colloid and Interface Science, 26, pp. 62-69 (1968).

Degussa AG: "Product Information Sipernat D 10", Dec. 2002, Internet: http://www.silica-library.com/SilicaWebAPP/pdf/PI_Sipernatd10_gb.pdf p. 1.

Wacker Chemie AG: "Silicones—there in more to it than you think. HDK-Pyrogenic silica", XP002534703 Internet: http://www.wacker.com/cms/media/publications/downloads/6174_EN.pdf pp. 6,7,9.

Degussa AG: "Product information Aerosil R202" Mar. 2004 XP002534704 Internet: http://birdchem.com/pdf/aerosil-r202.pdf p. 1.

Degussa: "Product Information Sipernat D17" Sep. 2004 Internet: http://www.silica-library.com//SilicaWebAPP/pdf/PI_Sipernatd17_gb.pdf whole document.

International Search Report dated Jun. 30, 2009 containing 132 pages.

* cited by examiner 1    2

1    2

FOAM MANIPULATION COMPOSITIONS CONTAINING FINE PARTICLES

CROSS REFERENCED TO RELATED APPLICATIONS

None

FIELD OF THE INVENTION

The present invention relates to foam manipulation compositions. In one aspect, the invention relates to stabilization compositions, and more particularly to the synergistic effect of fine particles and surfactant in lowering surfactant level requirements in foam generating consumer products without compromising properties desired by consumers of the products. In another aspect, the invention relates to defoaming compositions, preferably for consumer use, that collapse foams under rinse conditions.

BACKGROUND OF THE INVENTION

Consumers like foam producing products for a variety of personal and cleaning uses, such as laundry detergents, hand dish washing liquids, hard surface cleaners, hair and body shampoos, facial cleansers, shave preparation gels, and dentifrices. Foam based cleaning products create less mess and foam based personal care products have a pleasant feel. Consumers particularly like high and thick foams, quick foaming action, lasting foams, and the feel of rich, luxurious, creamy foams. To achieve these desirable effects, surfactants are added to many cleaning and personal care products. Surfactants play a major role in foam producing products by lowering the dynamic surface tension of the liquid-air interface to allow gas bubbles to be formed or introduced beneath the surface of the liquid. Surfactants also stabilize the foam once it is formed. However, surfactants are not without disadvantages.

The addition of surfactants adds to the cost of the final product. Further, there are environmental concerns associated with heavy use of some surfactants. Therefore, it is desirable to reduce the amount of surfactant in foam producing products, but without loss of the beneficial foaming properties surfactants offer.

The effect of particles on foamed products as reported in the literature has been inconsistent. Fine particles are known to be able to generate foams in the absence of a surfactant, probably by coating air bubbles and thereby minimizing interfacial fluid energy. However, some particles, such as hydrophobic famed silica in aggregate form of about 200 to 300 nm, are reported to function as defoaming agents.

U.S. Pat. No. 6,586,483 describes a foaming composition comprised of surface-modified, non-aggregated, inorganic nanoparticles, such as silica and titania, having a particle diameter of less than about 100 nm disposed in a vehicle, such as water or an organic liquid, with or without surfactant.

A foaming composition for use in cleansing the skin is described in U.S. Pat. No. 6,894,012. The composition contains at least one nonionic, anionic, amphoteric or zwitterionic foaming surfactant, 1% or more of silica particles of about 3 to 50 nm, an oxyalkylenated compound and one or more of a cationic or amphoteric polymer.

While high and thick foams are desirable, they have heretofore been difficult to rinse away without the use of excessive amounts of water or other rinse liquid. There is a tension between the desire for foaming products with good foam yield and the need to effectively rinse away the foam and avoid wasting water. In some areas of the world and at various times during the year, water conservation is of paramount importance.

The effect of fine particles in surfactant-based systems on foam generation and stability has not been fully elucidated in the literature. There does not appear to be any general understanding of how fine solid particles interact with surfactants during the process of foam generation.

SUMMARY OF THE INVENTION

The present invention provides a fine particle technology that permits the creation of foam manipulation compositions, which, in one aspect can boost foam formation and stabilize foams without compromising the desirable benefits obtained from foam products, such as foam volume and thickness, and in another aspect, can quickly reduce the level of foam under rinse conditions. A consumer product composition comprising a foam manipulation composition is provided. The foam manipulation composition is comprised of a plurality of surface-modified particles in combination with at least one surfactant. The particles have an average particle size greater than 100 nm and less than about 50 µm and a hydrophobicity measured by a contact angle between about 25° to 140°. The ratio of particles-to-surfactant may be between about 20:1 to about 1:20, and preferably 1:10.

In one embodiment, the foam manipulation composition is a foam stabilizing composition wherein the particles are silica nanoparticles having an average particle size greater than 100 nm up to about 600 nm, and preferably between about 200 nm and about 540 nm. In another embodiment, the particles are fine titania particles having an average size greater than 100 nm up to about 10 µm.

The composition may have a hydrophobicity as measured by a contact angle greater than 20°, and preferably greater than 28°, and more preferably in the range of about 25°-140°, and most preferably in the range 28°-100° or 40°-80°. In one example, particularly superior foam production and stabilization results were obtained wherein the hydrophobicity was expressed by a contact angle between about 58°-62°.

In one embodiment, the particles are solid particles selected from the group consisting of metal oxides, silica, titania, clay, mica, synthetic polymer particles, non woven polymers, starch, cellulose, proteins, and derivatives of starch, cellulose, and proteins, and combinations of organic and inorganic particles and combinations thereof.

The surfactant may be one selected from the group consisting of anionic, cationic, nonionic and amphoteric surfactants and combinations thereof.

In another aspect of the foam manipulation composition, the composition comprises a particulate component having switchable functional groups attached to the surface of the particles. The switchable functional groups are switchable upon exposure to a predetermined change in one or both of pH and temperature. The switchable functional groups are sensitive to one or both of pH and temperature changes and are easily protonated or deprotonated. The switchable functional groups may be Brønsted acids or bases on the surface of the particles. Alternatively, the switchable functional groups, such as carboxyl or amino groups, may be on compositions, such as polymers, grafted onto the surface of the particles.

A method for reducing the level of foam in a rinse solution is provided. Where the foamed product comprises particles in combination with at least one surfactant as described in the various embodiments herein, the surface of the particles is modified to include switchable functional groups. As stated above, the switchable functional groups are switchable upon exposure to a predetermined change in one or both of pH and temperature. The method for reducing the level of foam in a rinse solution includes defoaming the solution by one or more of the steps selected from (1) increasing the concentration of particles relative to surfactant and decreasing one of the pH or the temperature of the solution, and (2) increasing the size of the particles by aggregation of particles, (3) wherein at least one surfactant is an anionic surfactant and the step comprises reducing available anionic surfactants by forming one of a complex and (4) wherein at least one surfactant is an anionic surfactant and the step comprises reducing available anionic surfactants by forming a coacervate with positively charged particles by decreasing one of the pH or temperature of the rinse solution.

Defoaming by increasing the concentration of particles relative to surfactant may be done by adding a particulate powder, such as silica powder, to the product. Defoaming by increasing the concentration of particles relative to surfactant may be done by adding hydrophobic particles, such as milled and surface modified hydrophobic mica such as polydimethyl siloxane grafted mica, to the product at a basic pH, such as pH 10.

Defoaming by increasing the size of the particles may be done by adding particles having a high aspect ratio, such as fibers and platelets. Defoaming by decreasing the pH will occur, for example, under rinse conditions wherein the pH of the rinse solution is lower than the pH of the wash solution. This is particularly applicable to both liquid and granular forms of laundry detergents, dish washing detergents, or toothpaste wherein a polyacid functional group has been grafted onto the particles. The wash solution is typically alkaline, having a pH greater than 7. A rinse solution typically has a lower pH, such as the pH of tap water, about 7 and below. Protonation of the functional group, for example by grafting a polyacrylic acid that has pKa lower than 7, upon exposure to the lower pH in a rinse solution will dramatically increase the hydrophobicity of the particles that result in forming an antifoaming aggregate.

Examples of polymers that can be used as the switchable functional groups that are switchable upon exposure to a predetermined change in temperature may be, for example, polymers, which become insoluble (in other words hydrophobic) upon heating, have a so-called lower critical solution temperature (LCST). Polymers, which become soluble (in other words hydrophilic) upon heating, have an upper critical solution temperature (UCST). Typical LCST polymers are based on N-isopropylacrylamide (NIPAM), N,N-diethylacrylamide (DEAM), methylvinylether (MVE), and N-vinylcaprolactam (NVCl). A typical UCST system is based on a combination of acrylamide (AAm) and acrylic acid (AAc), and PEO-b-PPO, PEO-b-PPO-b-PEO and PEG-b-PLGA-b-PEG block copolymers. For example, an aqueous poly (NiPAAM) solution precipitates (i.e. becomes hydrophobic) above 32° C. (LCST) and the transition is very sharp.

BRIEF DESCRIPTION OF THE DRAWINGS

The various embodiments set forth in the Detailed Description of the Invention will be better understood with reference to the following non-limiting drawings, wherein.

DETAILED DESCRIPTION OF THE INVENTION

A. Definitions

Figure 1A:
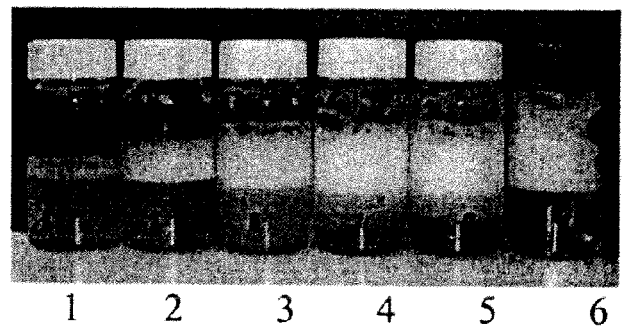
FIG. 1 shows the amount of foam produced by modified silica particles immediately after shaking (A) and after 4 days (B) from Example 2.

As used herein, the term "comprising" means various components conjointly employed in the preparation of the compositions of the present disclosure. Accordingly, the terms "consisting essentially of" and "consisting of" are embodied in the term "comprising".

As used herein, all percentages, parts and ratios are by weight of the total composition, unless otherwise specified. All such weights as they pertain to listed ingredients are based on the active level and, therefore do not include solvents or by-products that may be included in commercially available materials, unless otherwise specified.

The dimensions and values disclosed herein are not to be understood as being strictly limited to the exact numerical value recited. Instead, unless otherwise specified, each such dimension is intended to mean both the recited value and a functionally equivalent range surrounding that value. For example, a dimension disclosed as "40 mm" is intended to mean "about 40 mm". In this manner, slight variations above and below the stated ranges can be used to achieve substantially the same results as values within the ranges. Also, the disclosure of these ranges is intended as a continuous range including every value between the minimum and maximum values.

As used herein, "low-surfactant" means a surfactant concentration of 1%-20%, except for hand dish washing detergent and compacted detergents where the concentration is from 1%-45%.

"Consumer products" as used herein shall mean products made for use by consumers for personal care and home cleaning uses, including cleaning clothes, dishes and surfaces within the home or car. Exemplary consumer products include granular and liquid laundry detergents, liquid hand dish washing detergents, liquid hard surface cleaners, hair and body shampoos, shave preparation gels, facial cleaners, and dentifrices.

"Contact angle" with reference to hydrophobicity, as used herein, means the contact angle at the particle/air/liquid interface as measured using the gel trapping technique described by Paunov (Langmuir, 2003, Vol. 19, pp. 7970-7976) or by means of a commercially available goniometer (Rame-Hart, Inc. Model: 250-00-115) for measuring contact angles. The degree of hydrophobization of silica particles was characterized in terms of sessile drop contact angle with the nanoparticles layer cast onto a silicon wafer. Silicon wafers were first treated with cleaning solution (30% hydrogen peroxide, 30% ammonium hydroxide, and water in the ration 1:1:1) for 1 hour at 60° C. A few drops of the aqueous dispersion of hydrophobized nanoparticles were placed onto a silicon wafer and dried in an oven at 50-60° C. Then, the contact angle of a sessile water drop was measured in several different places and on different parallel samples.

"High aspect ratio" as used herein shall mean a high ratio of the square of the length, b, by the area, S, such that the aspect ration=$b^2$/S. A rod shaped molecule will have a high aspect ratio. The aspect ratio of a two dimensional shape is the ratio of its longer dimension to its shorter dimension. It is also applied to two characteristic dimensions of a three-dimensional object, particularly for the longest and shortest axes or for symmetrical objects (e.g. rods) that are described by just two measures (e.g., length and diameter).

"Hydrophobicity" as used herein shall mean the property of being water-repellent; tending to repel and not absorb water. Hydrophobicity increases with increasing contact angle.

"Foam Manipulation" as used herein shall mean one or more of the boosting or stabilization of foam in foam generating products under desired conditions, for example, under washing conditions, and the collapse or defoaming of foams under desired conditions, for example, under rinse conditions.

"Switching functional groups" as used herein shall mean any functional group that is sensitive to one or both of pH or temperature changes and is easily protonated or deprotonated. The switchable functional groups may be any functional group that acts as a Brønsted acids or bases and is grafted onto the surface of the particles, or may be on compositions, such as polymers, grafted or coated onto the surface of the particles. Examples of switchable functional groups include, but are not limited to, carboxyl or amino groups.

B. Description of Various Embodiments of the Invention

I. Improved Foaming

The synthesis and evaluation of surface active coated particles for use in surfactant-based systems for the production and stabilization of foam is described. The compositions described herein contain low surfactant levels and particles of a particle size, hydrophobicity, and material that provides a desirable level of foam production and unexpected improvement in foam stability over time. The compositions are suitable for use with formulations for various foam producing products. Formulations for use in particular products may also include, depending on the end use, polymers, builders, enzymes, fragrance, whitening agents, brightening agents, antimicrobial agents and softeners. The consumer products include, for example, high suds granules, high suds liquid laundry detergent, liquid hand dish washing detergent, liquid hard surface cleaners, hair and body shampoos, shave preparation gels, facial cleaners, and dentifrices.

The particles found to be particularly useful for maintaining or improving foaming properties while using low surfactant levels are surface modified particles having an average particle size greater than 100 nm and less than about 50 μm and a hydrophobicity measured by contact angle in the range of 25° to 140°. The hydrophobicity increases with the increase of the contact angle. In one embodiment, the average particle size is less than 10 μm and preferably less than about 2.1 μm. The particles are solid particles selected from the group consisting of metal oxides, silica, titania, clay, mica, synthetic polymer particles, non woven polymers, starch, cellulose, proteins, and derivatives of starch, cellulose, and proteins, and combinations of organic and inorganic particles and combinations thereof. The particles are typically hydrophilic particles which are treated as described herein to make them hydrophobic or amphiphilic, or to make them more or less hydrophilic. Particularly useful particles are hydrophobically modified silica and titania. However, hydrophobic particles such as non-woven polymers can also be surface treated to alter the degree of hydrophobicity, for example, to make then less hydrophobic to attain the desired contact angle in the range of 25° to 140°. Thus, the particles may be hydrophobic and surface modified by covalent attachment of a hydrophobic or hydrophilic layer thereto. Examples of hydrophobic attached particles include poly dimethyl siloxane and dimethyl silane. Examples of hydrophilic attached particles include polyethylene imine and polyacrylic acid.

The surfactants may be anionic, cationic, nonionic, amphoteric or combinations thereof.

Anionic surfactants may be selected from the group consisting of alkyl and alkyl ether sulfates, and alkyl benzene sulfonate. The alkyl ether sulfates are typically made as condensation products of ethylene oxide and monohydric alcohols having from about 8 to about 24 carbon atoms. Specific examples of alkyl ether sulfates which may be used in the cleansing phase of a product are sodium and ammonium salts of coconut alkyl triethylene glycol ether sulfate; tallow alkyl triethylene glycol ether sulfate, and tallow alkyl hexaoxyethylene sulfate. Highly preferred alkyl ether sulfates are those comprising a mixture of individual compounds, said mixture having an average alkyl chain length of from about 10 to about 16 carbon atoms and an average degree of ethoxylation of from about 1 to about 4 moles of ethylene oxide. Other suitable anionic surfactants include water-soluble salts of the organic, sulfuric acid reaction products of the general formula $R_1$—$SO_3$-M, wherein $R_1$ is chosen from the group consisting of a straight or branched chain, saturated aliphatic, and/or aromatic hydrocarbon radical having from about 8 to about 24, preferably about 10 to about 18, carbon atoms; and M is a cation. Suitable examples are the salts of an organic sulfuric acid reaction product of a hydrocarbon of the methane series, including iso-, neo-, meso-, n-paraffins, and alkyl benzene having about 8 to about 24 carbon atoms, preferably about 10 to about 18 carbon atoms and a sulfonating agent, e.g., $SO_3$, $H_2SO_4$, oleum, obtained according to known sulfonation methods, including bleaching and hydrolysis. Preferred are alkali metal and ammonium sulfonated $C_{10-18}$ n-paraffins.

Other suitable surfactants are described in McCutcheon's, Emulsifiers and Detergents 1989 Annual, published by M. C. Publishing Co., and in U.S. Pat. No. 3,929,678.

Preferred anionic surfactants for use in the cleansing phase include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, monoethanolamine cocoyl sulfate, sodium tridecyl benzene sulfonate, sodium dodecyl benzene sulfonate, and combinations thereof.

Anionic surfactants with branched alkyl chains such as sodium tridecyl sulfate, for example, are preferred in some embodiments. Mixtures of anionic surfactants may be used in some embodiments.

Cationic surfactants may be selected from tetra butyl ammonium bromide (TMAB).

Suitable nonionic surfactants include condensation products of alkylene oxide groups (hydrophilic in nature) with an organic hydrophobic compound, which may be aliphatic or alkyl aromatic in nature.

Amphoteric surfactants suitable for use in the cleansing phase include those that are broadly described as derivatives of aliphatic secondary and tertiary amines in which the aliphatic radical can be straight or branched chain and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecyl-aminopropionate, sodium 3-dodecylaminopropane sulfonate, sodium lauryl sarcosinate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and the products described in U.S. Pat. No. 2,528,378.

A typical formulation for use in laundry detergent may be comprised from 1%-50% surfactant, 0.02%-10% particles, 0.02%-10% polymers, and 1%-30% builders and other laundry adjuncts. A formulation for use in surface cleaners may be comprised of 1%-20% surfactant and 0.02%-5% particles plus conventional cleaning active components and adjuncts. A formulation for use in hair and body shampoos may be comprised of 1%-50% surfactant and 0.02%-5% particles plus conventional shampoo or body wash active ingredients and adjuncts. A formulation for use in dentifrices may be comprised of 1%-20% surfactant and 0.02%-5% particles together with conventional amounts of active ingredients and adjuncts.

While not wishing to be bound by any theory, it appears that the mechanism by which the addition of fine particles to a low surfactant-based foaming system boosts and stabilizes foams is by (1) reduction of the dynamic surface tension between the air/water interface; (2) migration to bubble walls of elastic surfactant membranes for increasing the film stability; and (3) slowing drainage by (a) gelation between bubbles; (b) increasing interfacial and/or bulk viscosity, and (c) steric repulsion.

EXPERIMENTS

A series of experiments were conducted to evaluate the effect of particles on foaming surfactant-based systems. In the first set of experiments, silica particles were modified to achieve samples with different degrees of surface hydrophobicity. The particles' foam stabilizing properties were characterized without the presence of surfactant. In these experiments, heterogeneous particles were synthesized which are capable of improving foam formation and foam stability even at low particle concentrations.

Materials and Equipment

Materials.

Silica particles: silica spheres of 150 and 420 nm in diameter were synthesized by the method describes in W. Stoeber et al., *Journal of Colloid Interface Science*, Vol. 26, No. 62 (1968).

Silica particles: AEROSIL 200 hydrophilic fumed silica, 200 $m^2$ per g purchased from Degussa DCDS: DiChloro DiMethyl Silane, purchased from Aldrich Additional Silica fumed nanoparticles were purchased from Sigma (S5505, Silica, fumed), particle size 0.014 μm, surface area: 200±25 $m^2$ per g.

(3-glycidoxypropyl)-trimethoxysilane (GPS) and poly(dimethylsiloxane) (PDMS), aminopropyl terminated (DMS-A32), Mw 30000 were purchased from Gelest, Inc.

Polyethyleneimine (PEI), water free, Mn 25000 by GCP was purchased from Aldrich.

Sodium dodecyl sulfate (SDS) was purchased from J.T Baker Inc.

Methylethylketone (MEK) was purchased from Aldrich.

Linear alkyl benzene sulfonic acid (LAS) was manufactured by The Procter & Gamble Company.

The following equipment was used in the experiments:
a particle size analyzer (Brookhaven, Model-90Plus);
an atomic force microscope (AFM) (Veeco, Model-Dimension 3000);
a goniometer (Rame-Hart, Inc); and
an imaging system (Model 250-00-115) for contact angle (CA) measurements

Example 1

Fabrication of Coated Silica Particles: Grafting of PDMS and PEI

PDMS (hydrophobic non-polar) and PEI (hydrophilic and polar) in water-toluene emulsions were used for grafting. The composition of the particle coating produced surface-active nanoparticles.

A1. Synthesis

The synthetic procedure starts with the covalent grafting of GPS to the silica surface via the reaction between the silanol groups on the silica surface and Si—$OCH_3$ groups of GPS. The hydrophilic-hydrophobic balance of the particle coatings was regulated by grafting PDMS and PEI in the second and the third steps, respectively. A range of samples were prepared with different compositions of the particle coatings regulated by grafting time. The surface composition of the particles was not evaluated quantitatively.

Silica nanoparticles (particle size: 0.014 μm, surface area: 200±25 m²/g) were dried in vacuum oven at 120° C. for 12 hours and then immediately used for silanization (see below). One gram of silica particles were dispersed in 200 mL of toluene in an ultrasonic bath for 2 hours. Two mL of GPS (3-(glycidoxipropyl)trimethoxysilane) was added to the dispersion and the mixture was stirred for 12 hours at room temperature. Afterward, the particles were isolated from the silanization mixture by centrifugation, re-dispersed in toluene, and centrifuged again. This washing process was repeated with toluene one more time. After the final centrifugation, the particles were re-dispersed in methyl ethyl ketone (MEK) with the concentration of the particles of 1%. In the next step, the GPS-modified particles (40 mL of 1% dispersion in the MEK) were mixed with 10% poly(dimethylsiloxane), aminopropyl terminated (Mw 30000). The mixture was heated in a water bath at 70° C. for 6 hours while being vigorously stirred. Thereafter, the dispersion was washed of its unreacted polymer by the centrifugation process described above. PDMS-grafted particle dispersion (1% in MEK) was divided into four parts. Each part was mixed with water free PEI (Mw 25000) at a concentration of 10% by weight. The mixtures were heated in a water bath at 70° C. while being vigorously stirred for a variety of times in order to achieve different PEI layer grafting densities. The particles were washed of unreacted PEI by the centrifugation process described above and then dispersed in deionized water obtained from Millipore Corporation containing 1% solids by weight.

A2. Characterization of Synthesized Particles

The polymer modified particles were characterized by dynamic light scattering (DLS) and the contact angle (CA) of the water. The characteristics of synthesized particles are presented in Table 1.

TABLE 1

Characteristics of the synthesized particles

| Sample | Original particle size, nm | Polymer coated particle size in water, nm | Contact angle on Si wafers, degree |
|---|---|---|---|
| A1 | 150 | 309 | 112.7 |
| A2 | 450 | 540 | 91.4 |
| B1 | 150 | 292 | 125.3 |
| B2 | 450 | 523 | 133.6 |
| B3 | 130 (aggregates) | 192 | 44.4 |

As can be seen from the DLS measurements, all samples show a slight aggregation of the particles in aqueous dispersions due to the hydrophobic interactions.

Coatings on silicon wafers were prepared from the water dispersions of the particles by casting and drying the samples in air. The water contact angles of the coatings are presented in Table 1. The samples A1, A2, B1 and B2 resulted in hydrophobic coatings. The sample B3 based on fumed silica resulted in a medium hydrophobic coating. As can be seen from the data, the particles have different hydrophobicity, and thus they have different ratios of polar and non-polar components

B. Preparation and Investigation of Particle Stabilized Foams

The Foaming Behavior and the Foam Stability

The particles-surfactant stabilized foams were formed by homogenizing 3 cm³ of an aqueous solution of 500 ppm SDS with added particle suspensions. The concentrations of the particles in the SDS solution were 100 ppm, 50 ppm and 30 ppm by solid at pH 6.4. In order to model a real washing formulation, the pH of the 30 ppm particle suspension was adjusted to pH 10.0 by the addition of NaOH. The foams were prepared in sample tubes (inner diameter: 1.5 cm, height 12 cm) by hand shaking for 2 min. The foaming was evaluated by measuring the foam height during 23 min. after shaking. The comparison of foam stability is shown in FIG. 7.

The data show that all particles samples improve foam production and the stability of foams as compared to the reference experiments with no particles. The best results were obtained with samples B2 and B3. For example, the sample B2 (450 nm silica spheres) produced a stable foam of 9.7 cm in height from the particle concentration of 30 ppm. This corresponds to an increase of the foam volume of about 32% as compared to the reference SDS aqueous solution. The medium hydrophobic particles (Sample B3) also resulted in the improved foam formation and foam stability In the second set of experiments, the effect of particle size, type, surface modification, and concentration were studied using several surfactants. The effect of type and concentration of surfactant, as well as particles-to-surfactant ratio was also investigated.

Characterization of Foam Stabilizing Ability of Modified Silica Nanoparticles (without Surfactant)

Example 2

In these Experiments, foam was generated by vigorous hand-shaking vials (20 ml capacity) containing 10 ml of sample for 10 seconds. Each set of samples was shaken simultaneously providing equal conditions for foam generation. The amount of foam and its stability was evaluated visually.

Five samples were prepared, containing Silica particles of different degrees of hydrophobicity: (1) 7-10°; (2) 16-20°; (3) 28-32°; (4) 40-45°; and (5) 58-62° (see Table 2 below and FIG. 1). Silica particles, 1% wt., were dispersed in MEK by ultrasonication for 60 min. Then, DCDS was added (1% vol.), and the dispersions were stirred for the time and temperature set forth in Table 2 below.

After stirring, the particles were centrifuged at 7500 rpm for 20 min and redispersed in the same amount of MEK. There were in total three cycles of centrifugation-redispersion. During the third cycle, the particles were redispersed in deionized (DI) water. With the increase of the degree of hydrophobicity of particles, the time of ultrasonication during redispersion in water increases and may take up to two days to fully redisperse the particles. Particles with higher hydrophobicity strongly tend to flocculate. In this case, the dispersion must be shaken or ultrasonicated for a few minutes before sample preparation. It was also observed that over time the hydrophobicity of particles dispersed in aqueous medium may decrease. It was also found that it was difficult to modify the surfaces of the smaller particles, particularly those particles having an average diameter of 100 nm or less. When the particle size was increased to an average diameter 200 nm, the surface modification worked well.

TABLE 2

Experimental conditions and corresponding contact angle

| | Time, hours | Temperature | Contact angle | Particle Size |
|---|---|---|---|---|
| 1 | 1 | room | 7-10° | 200 nm |
| 2 | 5 | room | 16-20° | 200 nm |

TABLE 2-continued

Experimental conditions and corresponding contact angle

| Time, hours | Temperature | Contact angle | Particle Size |
|---|---|---|---|
| 3 | 15 | room | 28-32° | 200 nm |
| 4 | 3 | 60 | 40-45° | 200 nm |
| 5 | 6 | 60 | 58-62° | 200 nm |

Figure 1B:
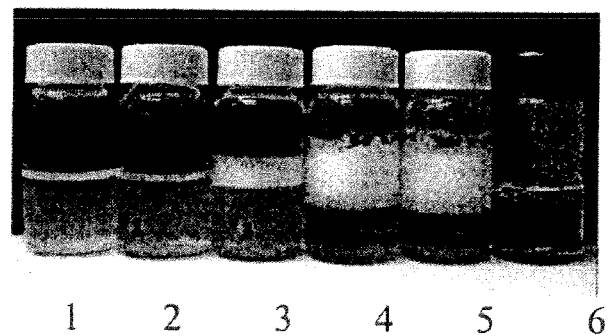

A surfactant solution containing 300 ppm of LAS (6) was used as a reference. The amount of foam produced upon hand-shaking correlated with the degree of hydrophobicity of the silica particles. As shown in FIG. 1a, the highest amount of foam was produced by the sample with the most hydrophobic particles. Foam stability correlated with the degree of hydrophobicity as well. Foam produced by the first two samples with low hydrophobicity disappeared in a few hours. On the other hand, foam generated by the more hydrophobic particles remained even after 4 days, as shown in FIG. 1b.

Effect of Fine Particles on Foam Generation and Stability in the Presence of Surfactant A. Hydrophilic Particles with Anionic Surfactant Example 3

The effect of hydrophilic silica particles of different sizes on foaming in the presence of an anionic surfactant, linear alkyl benzene sulfonic acid (LAS), was evaluated using a hand-shake experiment in the manner described above. The particles sizes ranged from an average diameter of 20 nm, 200 nm, and 1.75 μm for silica and an average diameter of 2.1 μm for titania. The samples are shown in FIG. 2 in vials marked 1, 2, 3 and 4, respectively. A solution of the surfactant, LAS at 100 ppm was used as a reference and is shown as vial 5 in FIG. 2. The concentration of particles in vials 1 through 4 was 1000 ppm.

Figure 2A:
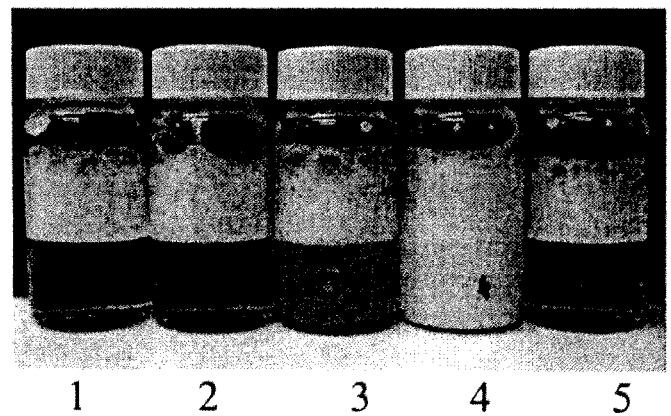
FIG. 2 shows the amount of foam produced by anionic surfactant in the presence of hydrophilic particles immediately after shaking (A) and after 5 hours (B) from Example 3.
Figure 2B:
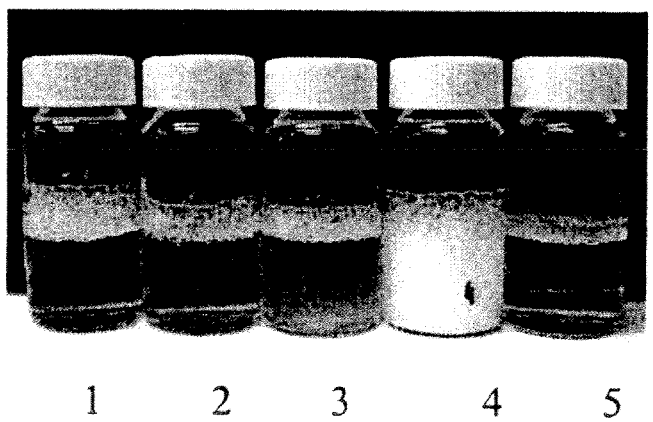
Figure 3A:
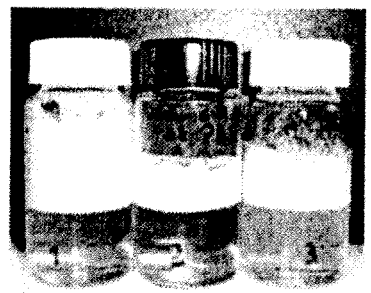
FIG. 3 shows the amount of foam generated by a combined surfactant/particles system (vial 1), surfactant alone (vial 2), and particles alone (vial 3) immediately after shaking (A), and after 16 hours (B) from Example 4.
Figure 3B:
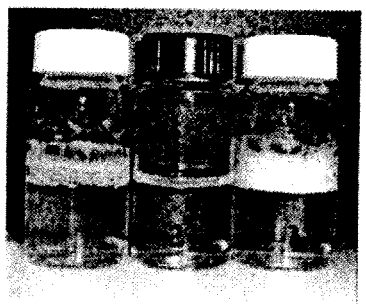

All of the samples that contained particles produced almost the same amount of foam, which was slightly higher than the amount of foam produced by LAS alone (see, FIG. 2a). After five hours, as shown in FIG. 2b, the difference became even more pronounced, demonstrating that the presence of the particles improves the stability of the foam produced by an anionic surfactant. Small silica particles (20 nm) and titania particles (2.1 μm) created more stable foam than the 200 nm and 1.75 μm silica particles, but all samples with particles retained some foam.

B. Hydrophobized Particles with Anionic Surfactant

Example 4

Silica samples having a hydrophobicity measured at a contact angle of 58-62° were used to study the effect of hydrophobized particles. The foaming of particles with the surfactant, LAS was compared to the foaming of particles alone and the foaming of particles with LAS alone. The concentration of particles was 1000 ppm and the concentration of LAS was 30 ppm. After shaking, the amount of foam produced by the combined surfactant/particles system was significantly higher than that produced by particles alone or surfactant alone. This suggests that in the combined system, both the surfactant and the particles may participate in foam stabilization. After 16 hours, the foam generated by the surfactant disappeared, the foam generated by the combined system decreased by 85%-90%, and the amount of foam generated by the particles alone decreased only slightly. This observation shows that the foam generated by combined surfactant/hydrophobic particles system is more stable than the foam produced by surfactant alone, but less stable than the foam produced by hydrophobized particles alone.

Example 5

Figure 4A:
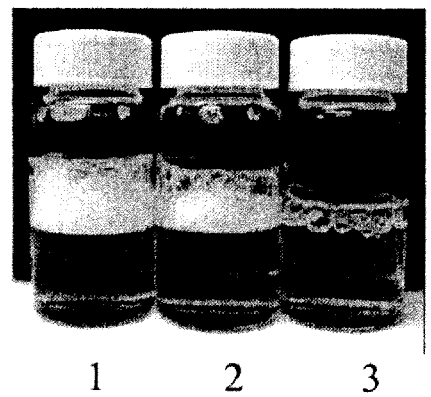
FIG. 4 shows the amount of foam generated by a combined surfactant/particles system (vial 1), surfactant alone (vial 2), and particles alone (vial 3) in three compositions from Example 5.
Figure 4B:
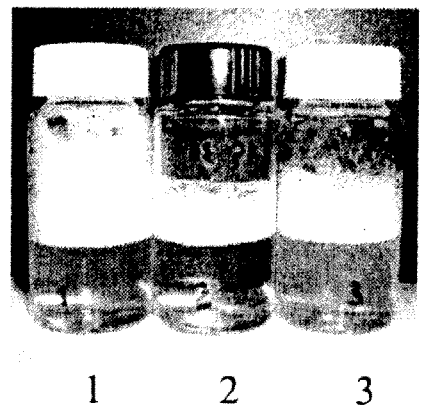
Figure 4C:
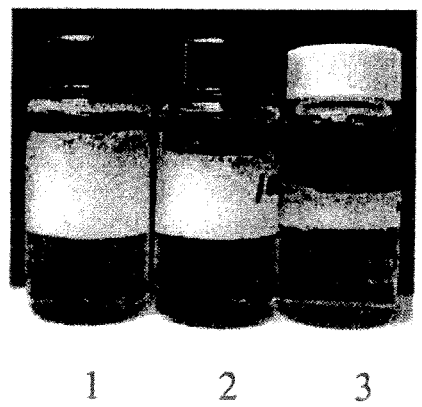

In this experiment, the effect of surfactant and particle concentration and particles-to-surfactant ratio was studied. The comparisons are shown in FIG. 4. Three combined systems with different concentrations of components were studied: A) LAS 30 ppm, Silica 100 ppm; B) LAS 100 ppm, Silica 1000 ppm; C) LAS 100 ppm, Silica 300 ppm (vials 1 of FIG. 4). Each combined system was compared to solutions containing surfactant only (vials 2 of FIG. 4) and particles only (vials 3 of FIG. 4) at the same concentration as in the combined surfactant/particle systems. The amount of foam produced in each case was greater with the combined system, but the synergy achieved by the combination of surfactant and particles was most pronounced in the system B, where the particles-to-surfactant ratio was the highest, 10 to 1.

Example 6

Figure 5A:
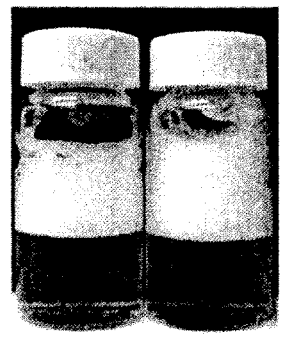
FIG. 5 shows the amount of foam generated by combined surfactant/particles system with a concentration of 1000 ppm silica to 30 ppm surfactant (vial 1) and 1000 ppm silica to 100 ppm surfactant (vial 2) immediately after shaking (A) and after 5 hours (B) from Example 6.
Figure 5B:
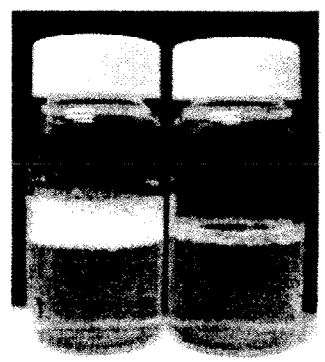

In this experiment, the effect of surfactant concentration on foam stability in the combined surfactant/particles system was studied. Two samples were compared where the concentration of silica particles was the same (1000 ppm), and the concentration of LAS was 30 ppm (sample 1, FIG. 5) and 100 ppm (sample 2, FIG. 5). Immediately after shaking, the amount of foam in sample 2 was slightly higher due to significantly higher surfactant concentration. Surprisingly, however, after 5 hours, the foam in sample 2 almost disappeared, whereas in sample 1 approximately 40% of the foam remained. This result shows that the stability of the foam generated by the combined surfactant/hydrophobized particles system decreases with the increase of surfactant concentration. While not wishing to be bound by theory, one possible reason for this result may be that the surfactant competes with the particles for the adsorption at the air/water interface.

C. Hydrophilic Particles with Cationic Surfactant

Example 7

Figure 6A:
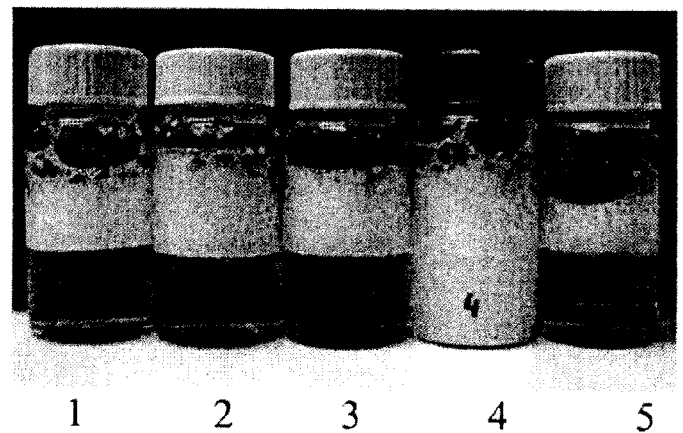
FIG. 6 shows the amount of foam produced by cationic surfactant in the presence of hydrophilic particles immediately after shaking (A) and after 4 hours (B) from Example 7.
Figure 6B:
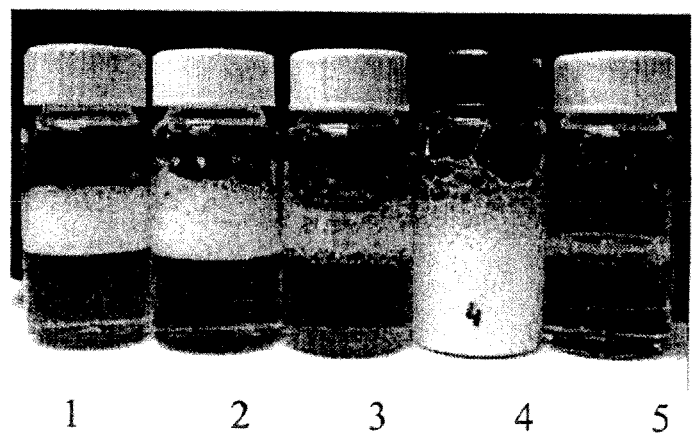
Figure 7A:
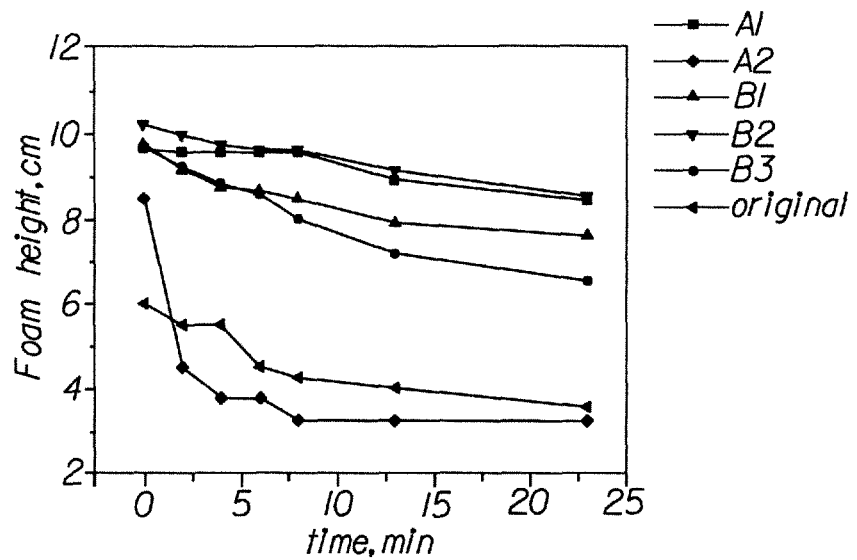
FIGS. 7(*a*)-(*d*) are graphs comparing the height of foams vs. time (after shaking) produced from 3 cm$^3$ of water in the presence of SDS (500 ppm) at pH 6.4 and synthesized particles at concentrations of 100 ppm (a); 50 ppm (b), and 30 ppm (c), and at pH 10 at particle concentration of 30 ppm (d) as described in Example 1.
Figure 7B:
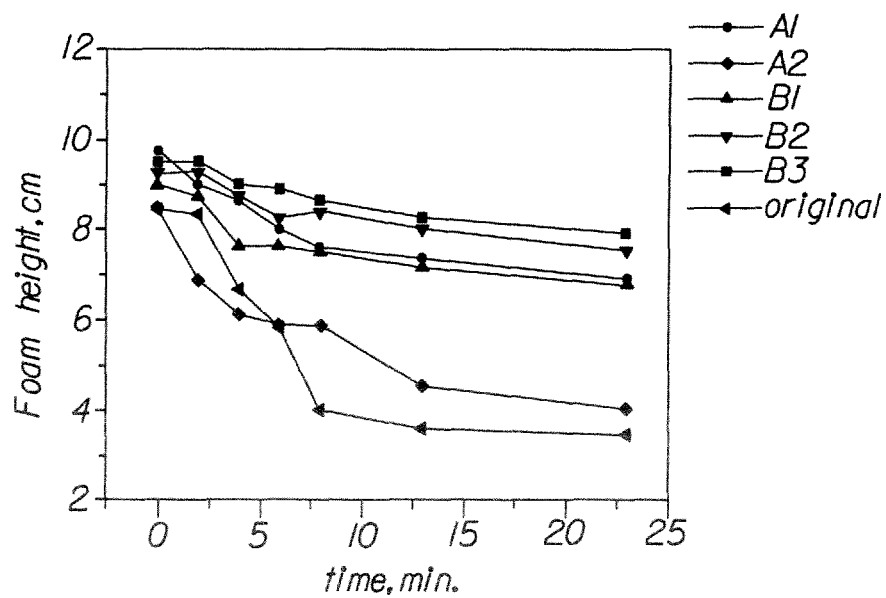
Figure 7C:
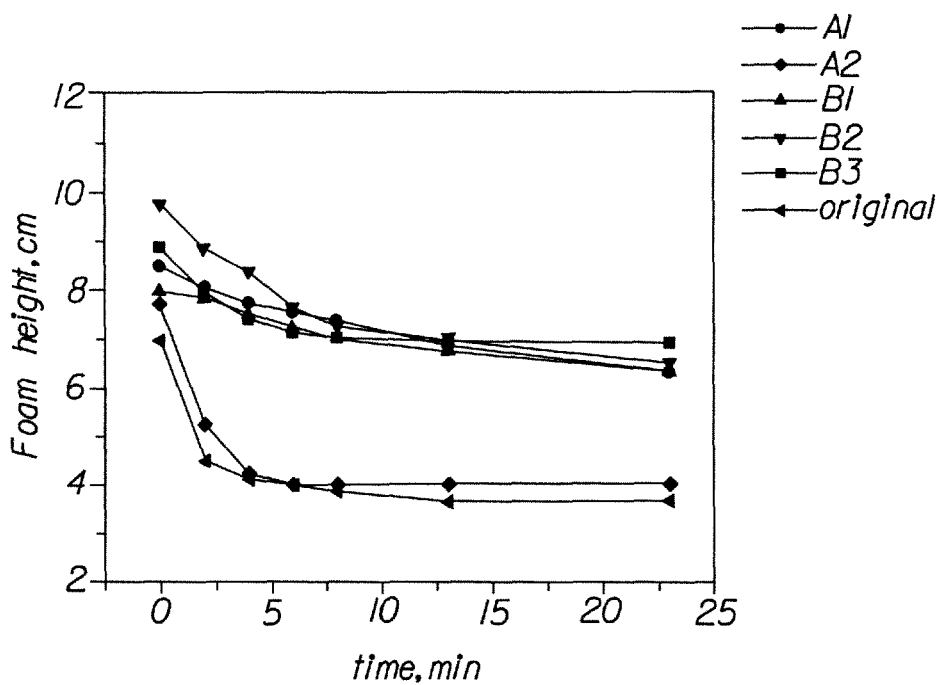
Figure 7D:
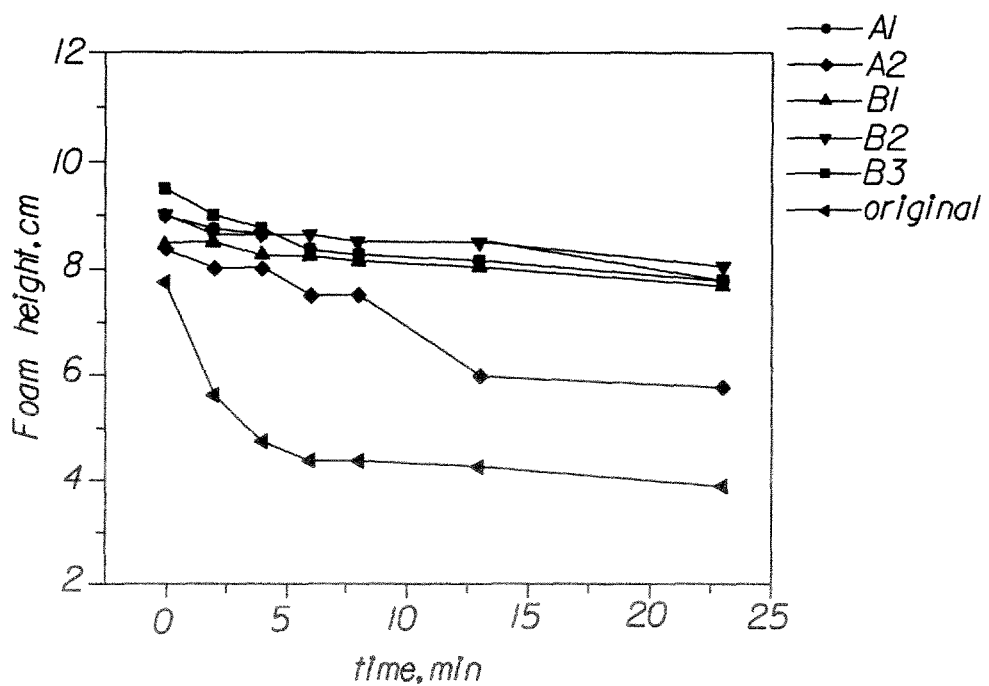

The effect of hydrophilic silica particles of different sizes (20 nm, 200 nm, and 1.75 μm) and titania particles of 2.1 μm size (see FIG. 6, vials 1, 2, 3 and 4, respectively) on foaming in the presence of a cationic surfactant, tetra methyl ammonium bromide (TMAB), was evaluated using the same hand-shake experiment described above. The concentration of TMAB was 100 ppm and the concentration of particles was 1000 ppm. The solution of TMAB 100 ppm was used as a reference (see FIG. 6, vial 5). All samples containing particles produces significantly larger amounts of foam than the samples containing TMAB only. While not wishing to be bound by theory, it is believed that the cationic surfactant adsorbs onto the surface of negatively charged particles and, thus, makes them more hydrophobic. The beneficial result is an increase in the amount of foam produced and the stability of the foam so produced. As shown in FIG. 6, samples with 200 nm silica and 2.1 μm titania particles produced more foam than 20 nm and 1.75 μm silica, respectively. It was surprisingly found that the stability of the foam produced by particles with cationic surfactant was significantly higher than that produce by surfactant alone. After four hours, the foam from cationic surfactant alone disappeared, whereas the foam in all samples containing particles remained. The 20 nm silica particles produced the most stable foam with the lowest rate of coalescence, and the 1.75 µm silica particles produced the least stable foam. These are hydrophilic particles without surface modification. As shown in the test condition, high level (1000 ppm) particles are required to boosting foams.

The examples above describe the synthesis of heterogeneously coated particles and the investigation of the particle-surfactant stabilized foams. The synthesized heterogeneous particles improved the foam formation and the foam stability in the formulations with sodium dodecyl sulfate (SDS) even at low particle concentrations.

Example 7 above and Example 8 below demonstrate that surfactant/particles ratios greater than 5:1 and close to 10:1 can be achieved.

The following observations can be made based on the foregoing experiments. The combination of particles and levels of surfactant lower than those typically found in foam producing products produced longer lasting foam than surfactant alone. For systems with hydrophilic nanoparticles and anionic surfactant, hydrophilic particles exhibit small boosting and stabilizing effect on the foam generated by anionic surfactant, particles of smaller size in most cases show superior performance, and titania particles are more effective than silica of the same size.

For systems with hydrophobized nanoparticles and anionic surfactant, moderately hydrophobic silica particles at suitable particles-to-surfactant ratio (1:10) significantly increase the amount of foam and the stability of the foam, foam generated by the combined particles/surfactant system is more stable than the foam produced by surfactant only, but less stable than the foam produced by particles alone, and in the combined surfactant particles systems, the stability of the foam increases with the increase of particles-to-surfactant ratio.

For systems with hydrophilic nanoparticles and cationic surfactant, hydrophilic silica particles with cationic surfactant significantly increase both amount of foam and the stability of the foam, the effect of the particles increases as the size of the particles decreases, and titania particles are more effective than silica particles of the same size.

The following examples arose from the investigation of the foam formations and the foam stability in the particle-surfactant formulations. The surfactant used was p-alkylbenzene sulfonic acid (LAS) was provided by The Procter & Gamble Company.

The synthesis and the particle characteristics were described in the Examples above. Briefly, the synthesized particles (Samples A1 and B1 based on 150 nm silica spheres; A2 and B2 based on 420 nm silica spheres, and B3 based on fumed silica particles) have different hydrophobic-hydrophilic balance due to patterns onto the particle surface, and thus, the particles have different ratios of polar and non-polar components. That effect was used to stabilize aqueous foams.

Example 8

Particle-Surfactant Formulations at pH10

The particles-surfactant stabilized foams were formed by homogenizing 2 cm$^3$ of an aqueous solution of LAS of a concentration of 300 ppm with added particle suspensions. The concentrations of the particles in the LAS solution were 30 ppm, 45 ppm, and 100 ppm by solid at pH 10 (adjusted with NaOH). The foams were prepared in sample tubes (inner diameter: 1.5 cm, height: 12 cm) by hand shaking for 2 min. The foaming was evaluated by measuring the foam height during 20 min after homogenizing and was compared with the reference LAS solutions at 300 ppm and 500 ppm at pH10. FIG. 8 represents the data of the foaming behavior and the foam stability of the LAS-particles formulations with the particles concentrations of 30 ppm, 45 ppm, and 100 ppm at pH 10.

Figure 8A:
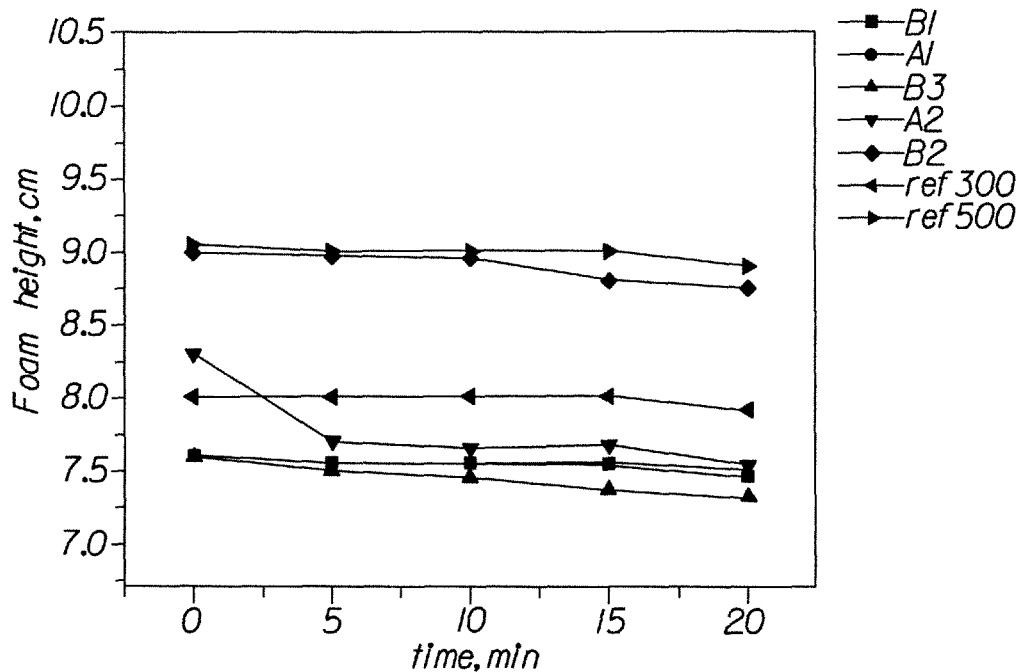
FIGS. 8(*a*), (*b*) and (*c*) are graphs showing the height of foams over time after agitation produced with a combined surfactant/particle system at pH 10 and synthesized particles at concentrations of 30 ppm (a); 45 ppm (b), and 100 ppm (c)
Figure 8B:
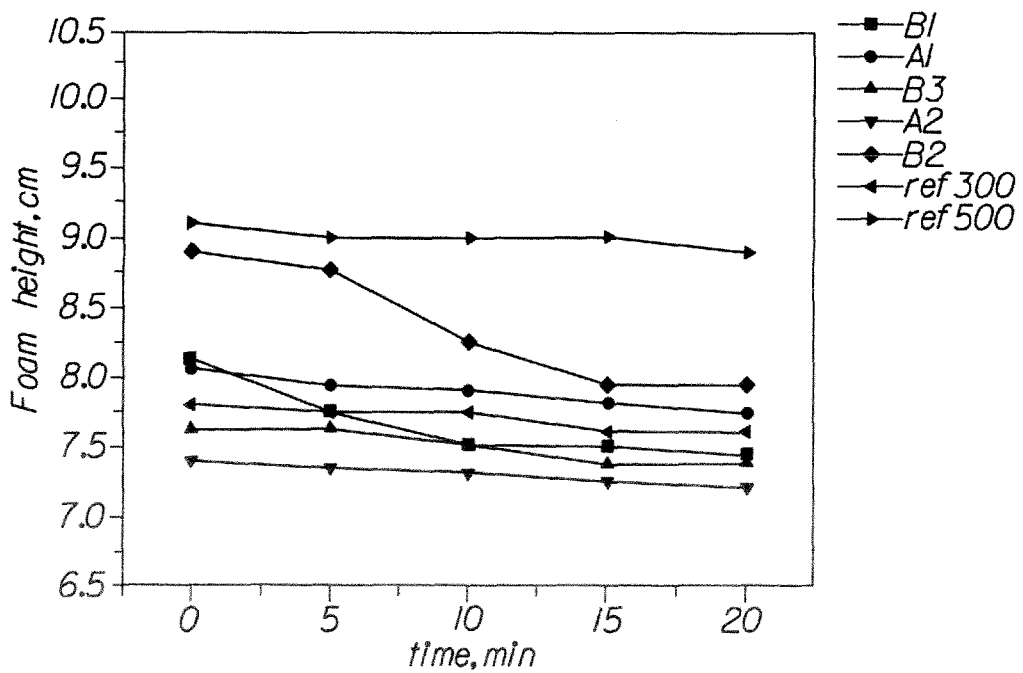
Figure 8C:
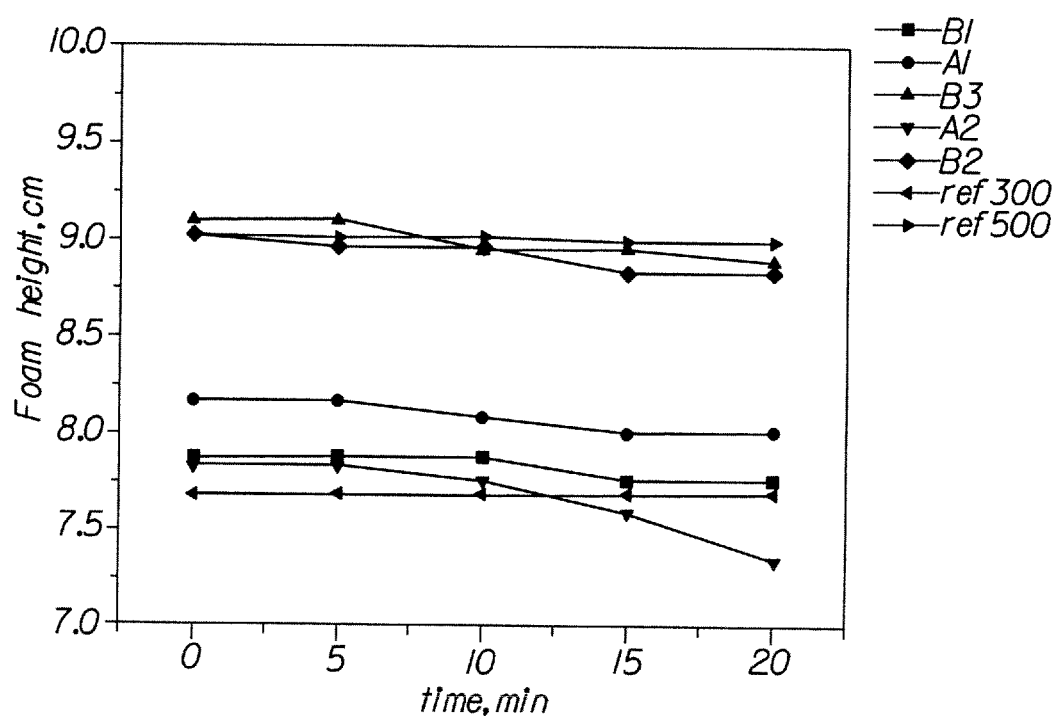

As illustrated from the data presented in FIG. 8, all particles readily stabilized foams right after agitation at the concentration of 100 ppm in the surfactant-particle formulations (FIG. 8c). Samples B2 and B3, which correspond to fumed silica and 420 nm silica spheres with the water contact angle values of 44.4° and 133.6°, respectively, showed the best stabilizations of foams, similar to the reference LAS sample at 500 ppm. Sample B2 also sufficiently improved the foam formation at the particles' concentrations at 30 ppm and 45 ppm. The foam height values of the sample were close to those of the reference 500 ppm sample. (FIGS. 8a, b). Thus, the sample demonstrated the improvement of the foam formation in the particle-surfactant formulations at pH 10. Not wishing to be bound by any theory, the result may be attributed to the appropriate particle chemical surface composition as well as to the developed surface of the particles and shape (fumed silica) that appear to be necessary for the particle adsorption at the air liquid interface.

II. Improved Defoaming

Example 9

Particle-Surfactant Formulations at pH 6

The experiment was performed in the same way as described above. FIG. 9 represents the data of the foaming behavior and the foam stability of the LAS-particles formulations with the particles concentrations of 30 ppm, 45 ppm, and 100 ppm at pH 6.

Figure 9A:
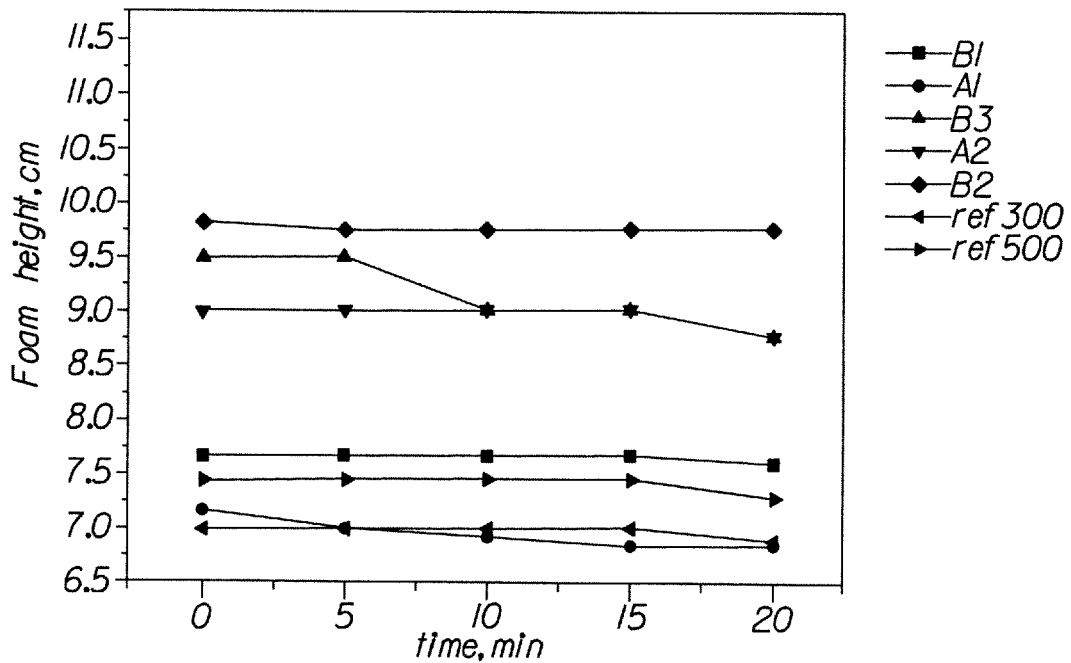
FIGS. 9(*a*), (*b*) and (*c*) are graphs showing the height of foams over time after agitation in a combined surfactant/particle system at pH 6 and synthesized particles at concentrations of 30 ppm (a); 45 ppm (b), and 100 ppm (c)
Figure 9B:
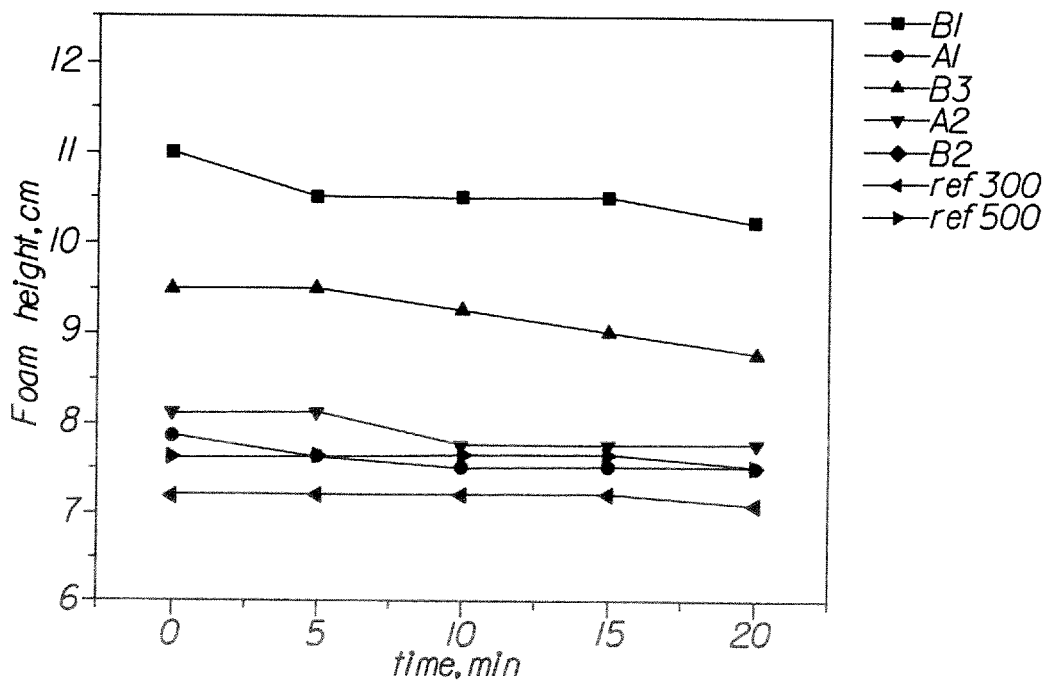
Figure 9C:
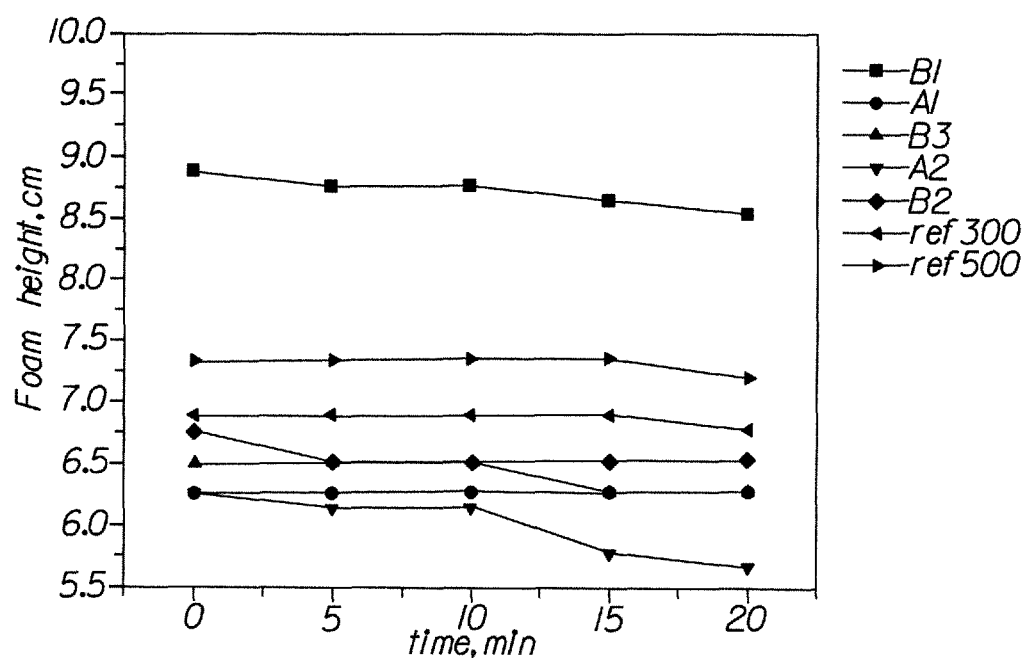

The results shown in FIG. 9 indicate that the particles raise the foam formation in the formulations at the low particle concentrations of 30 ppm at pH6 (FIG. 9a). However, an increase in the contribution of almost all samples to defoaming is observed for the higher particle concentrations of 45 ppm and 100 ppm (FIGS. 9b, c). The contribution of sample B1 to stabilizing the foams at the higher particle concentrations remains fairly high. These findings indicate that the particles foaming-defoaming properties strongly depend on pH and the particle concentrations in the surfactant formulations. The particle shell consists of the grafted non-polar PDSM and polar PEI. PEI is a weak basic polyelectrolyte (pKa=8.8), thus its surface activity and degree of ionization are strongly pH dependant. In general, foam formation was favored by increasing the positive charge onto PEI by decreasing the suspensions' pH at low particle concentrations (FIGS. 9b, c), whereas defoaming was favored by increasing the particle concentration. Again, not wishing to be bound by theory, such trends may be explained by the fact that a decrease in pH results in an increase of the particle surface activity that enables their adsorption to the air-liquid interface and the stabilization of foams. At the same time, the positively charged particles interact with the negatively charged LAS in the particle surfactant suspensions, thus an increase in the particle concentration inevitably reduces the concentration of the free (non-adsorbed to the particle surface) surfactant that leads to a small amount of foam. Protonation of the particles also leads to particle aggregates of a larger size that play an antifoaming role by breaking lamellae via a spreading or a "bridging-dewetting" mechanism.

Therefore, to improve the particle defoaming properties at low pHs, polyacids should be used instead of polybases (PEI). It is understood that by selecting a specific polymer system with a predetermined pKa, preferably from pKa 3-11, defoaming properties can be optimized based on the particular application. The estimated pKa values are based on the pKa of the functional group on the particle or the composition coated on the particle and can be measured using well known pH titration methods, such as those disclosed in A. Albert and E. P. Seargent, "The Determination of Ionisation Constants—A laboratory Manual," $3^{rd}$ Ed., Chapman and Hill (1984). For laundry applications, an exemplary target pKa is about 8. For hand dish detergent applications, the target pKa is about 7-11. For hair and body shampoos, dentifrices, hard surface cleaning, facial cleanser and shaving preparations, the target pKa is about 6-11.

Examples of polymers that can be used as the switchable functional groups that are switchable upon exposure to a predetermined change in temperature may be, for example, polymers, which become insoluble (in other words hydrophobic) upon heating, have a so-called lower critical solution temperature (LCST). Polymers, which become soluble (in other words hydrophilic) upon heating, have an upper critical solution temperature (UCST). Typical LCST polymers are based on N-isopropylacrylamide (NIPAM), N,N-diethylacrylamide (DEAM), methylvinylether (MVE), and N-vinylcaprolactam (NVCl). A typical UCST system is based on a combination of acrylamide (AAm) and acrylic acid (AAc), and PEO-b-PPO, PEO-b-PPO-b-PEO and PEG-b-PLGA-b-PEG block copolymers. For example, an aqueous poly (NiPAAM) solution precipitates (i.e. becomes hydrophobic) above 32° C. (LCST) and the transition is very sharp.

These examples demonstrate that synthesized heterogeneous particles are capable of stabilizing the foams in the particle-LAS formulations at pH10 even at low particle concentrations.

Development of Defoaming Agent for System Based on Linear Alkylbenzylsulfonate (LAS)

Example 10

Investigation of Defoaming Effect of Binary PDMS-PAA System Grafted onto Silica Particles Materials:
Sample DF2 (600 nm silica particles with grafted binary PDMS-PAA brush; synthesis of this sample was described above in Example 1.)
Linear Alkylbenzene Sulfonate, Acidic Form (LAS)

Defoaming experiments were done by shaking 2 ml of a solution for 2 min in a 15 ml centrifuge tube with internal diameter of 1.5 cm. Shaking frequency was about 2 shakings per second. The foam volume recorded is a total volume of liquid plus foam. Results of shake-tests are presented in Table 3.

TABLE 3

Results of shake-tests of the samples containing LAS and DF2 at various concentrations and pH

| | LAS, ppm | DF2, ppm | pH | Foam volume, ml |
|---|---|---|---|---|
| Reference | 300 | — | 10 | 8.4 ± 0.4 |
| | | — | 4 | 8.3 ± 0.4 |
| | 300 | 300 | 10 | 8.4 ± 0.4 |
| | | 1000 | 10 | 8.8 ± 0.3 |
| | 300 | 300 | 6 | 8.6 ± 0.3 |
| | | 1000 | 6 | 8.9 ± 0.3 |
| | 300 | 300 | 4 | 8.0 ± 0.3 |
| | 300 | 1000 | 4 | 8.2 ± 0.3 |

During time interval of 20 min foam volume remained the same.

From the results presented above, it can be seen that in the system with LAS as a surfactant, the effect of the modified silica particles is small, possibly because LAS is a more active surfactant than SDS. The defoaming effect of particles can be increased by increasing hydrophobicity, size or using particles with high aspect ratio, like fibers or platelets.

Highly hydrophobic amorphous silica, obtained from Gelest Inc., was used as particles with higher hydrophobicity. Milled mica was uses as particles of a larger size and higher aspect ratio.

Example 11

Investigation of Defoaming Effect of Hydrophobic Amorphous Silica

Materials:
1. Amorphous silica, octamethylcyclotetrasiloxane treated, SI 56961.0, Gelest Inc. Average diameter 200 nm.
2. LAS Experimental procedure: Two methods were used for defoaming experiments.

Method 1. Silica particles were first dispersed in 1% LAS solution by ultrasonication for 8 hours. This dispersion was used for mixing with LAS solution.

Method 2. Silica particles were added as a powder to the surfactant solution and then the solution was shaken. The silica was not dispersed in water. The Results of shake tests are summarized in Table 4.

TABLE 4

Results of shake tests of samples containing LAS and hydrophobic amorphous silica

| | LAS, ppm | Silica, ppm | pH | Foam volume, ml |
|---|---|---|---|---|
| Reference | 300 | — | 10 | 8.3 ± 0.5 |
| Method 1 | 300 | 500 | 10 | 8.0 ± 0.4 |
| | | 1000 | 10 | 7.8 ± 0.5 |
| Method 2 | 300 | 500 | 10 | 6.0 ± 0.5 |
| | | 1000 | 10 | 3.5 ± 0.3 |

During time interval of 20 min foam volume remained the same.

As we can see from the results in Table 4, hydrophobic amorphous silica is more effective as a defoaming agent when it is not dispersed in water prior to the shake-test. While not wishing to be bound by theory, this result may be due to the decrease of hydrophobicity of the particles upon exposure to aqueous medium for prolonged time.

Example 12

Investigation of Defoaming Effect of Hydrophobized Mica Particles

Figure 10A:
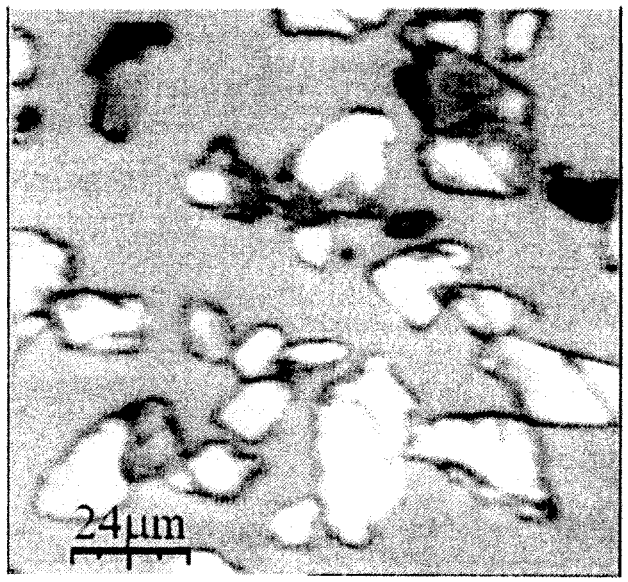
FIG. 10 shows optical images of milled mica.
Figure 10B:
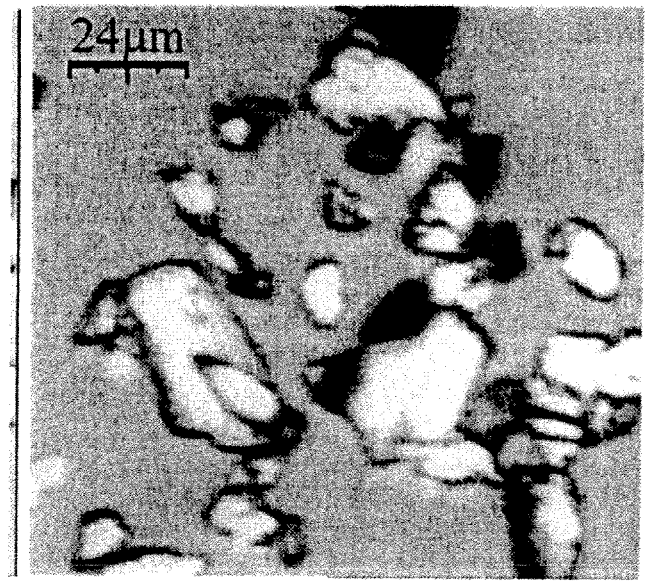
Figure 11A:
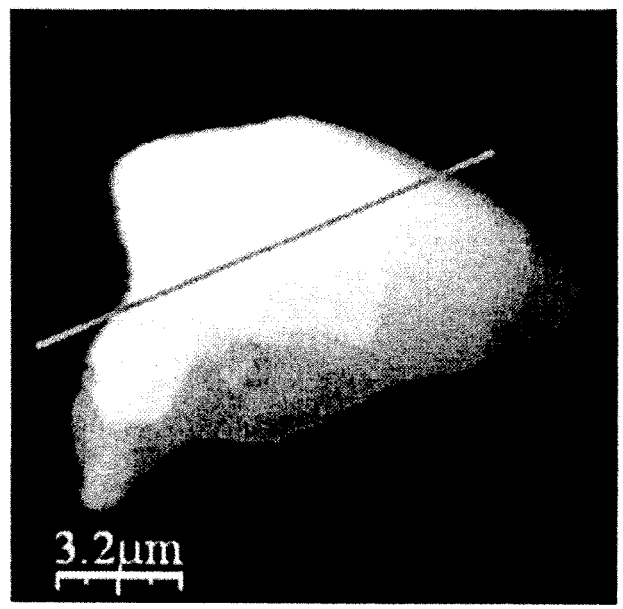
FIG. 11 shows the AMF topography image and cross-section of a mica flake.
Figure 11B:
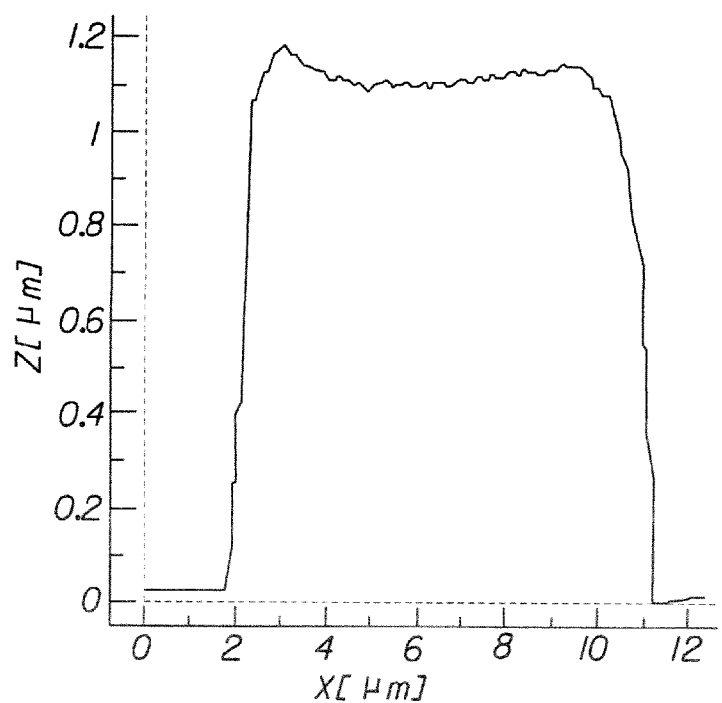

Milled mica flakes having a broad size distribution ranging on average from 1 to 30 microns, and a thickness ranging from 400-1200 nm, as estimated using AFM (FIGS. 10 and 11) were used.

Materials:
Milled mica, Sky Chemical Co Ltd.
(Epoxycyclohexylethyl)-methyl siloxane-dimethylsiloxane copolymer (ECMS-924), Gelest Methylethylketone, (MEK)
Linear alkylbenzylsulfonate, acidic form (HLAS)

Hydrophobization of mica particles was performed in one step, using PDMS copolymer, which contains 8-10% monomer units with epoxy-group in side chain. Epoxy-groups react with hydroxyl-groups, which are present on mica surface.

Hydrophobization Procedure:
Sample DFM1

One hundred mg of milled mica was washed in chloroform by ultrasonication for 1 hour to remove any organic impurities. After that, mica was dispersed in 10 ml of MEK and transferred into 50 ml round-bottom flask. Further, 0.5 g of ECMS-924 was added and the dispersion was manually stirred until the polymer dissolved. The solvent was then evaporated using vacuum rotary evaporator. The flask was placed into the oven at 125° C. under vacuum for 16 hours. Then, 15 ml of MEK was added and the flask was stirred until the particles dispersed and ungrafted polymer dissolved. The particles were cleaned from ungrafted polymer by triple centrifugation and redispersion in fresh MEK. Then, the dispersion was centrifuged again, the solvent was decanted, and the particles were dried in the oven at 60° C. for 3 hours.

Contact Angle of the Cast Layer Formed by the Particles: 115-120°.

Example 13

Defoaming Experiments

Figure 12:
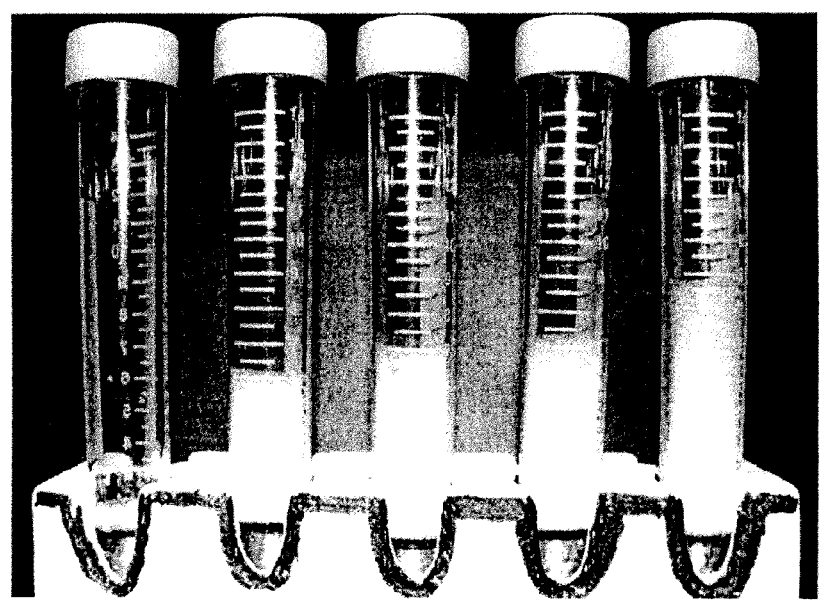
FIG. 12 shows the initial foam volume after shaking of samples containing 300 ppm of LAS as surfactant and, from left to right, 300 ppm, 100 ppm, 60 ppm, 30 ppm, and 0 ppm of mica at pH 10; and, FIG. 13 is a bar graph of the samples of FIG. 12 showing foam plus the original liquid volume obtained after shaking the samples.
Figure 13:
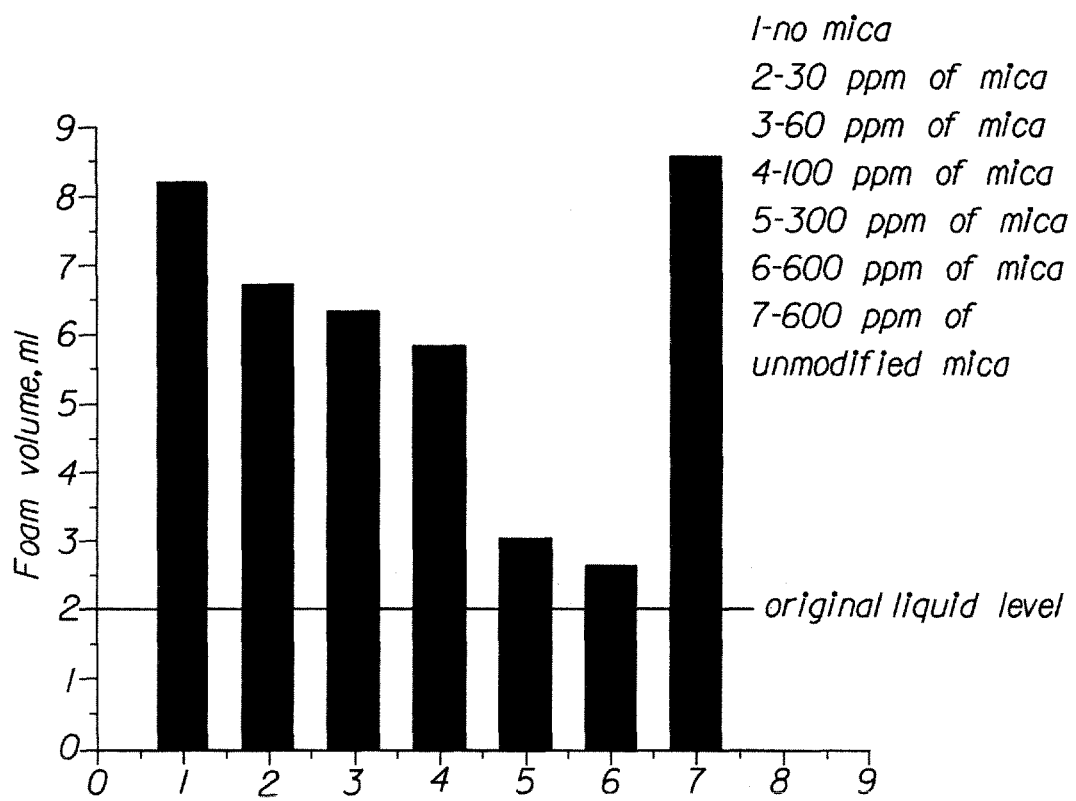

Dried hydrophobized mica particles were easily dispersed in aqueous LAS solution. The concentration of the surfactant (LAS) was 300 ppm. The pH was adjusted to 10. FIGS. 12 and 13 show the foam volume immediately after shaking the samples.

From FIG. 13, it can be seen that hydrophobized mica particles can effectively decrease foaming of LAS, whereas original unmodified mica does not cause any effect on foaming. It can be concluded, therefore, that hydrophobized milled mica appear to be a most effective defoaming agent.

All documents cited in the Detailed Description of the Invention are, in relevant part, incorporated herein by reference, the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

The invention claimed is:

1. A foam manipulation composition comprising:
   from 0.02% to 10% by weight of the composition of a plurality of surface-modified particles, wherein said particles are modified by grafting a polydimethylsiloxane and a polyethyleneimine to the surface of the particle, the surface-modified particles having an average particle size greater than 100 nm up to about 50 μm and a hydrophobicity measured by a contact angle greater than 20°; and
   at least one surfactant, the surface-modified particles and the at least one surfactant being present in a ratio of particles to surfactant of between about 1:20 to 20:1.

2. The composition recited in claim 1 wherein the ratio of particles-to-surfactant is between about 1:10 to about 10:1.

3. The composition recited in claim 1 wherein the contact angle is in the range between about 25° to 140°.

4. The composition recited in claim 1 wherein the particles are solid particles selected from the group consisting of metal oxides, silica, titania, clay, mica, synthetic polymer particles, non woven polymers, starch, cellulose, proteins, and combinations thereof.

5. The composition recited in claim 4 wherein the particles are silica.

6. The composition recited in claim 4 wherein the particles are titania and the average particle size is greater than 100 nm up to about 10 μm.

7. The composition recited in claim 1 wherein the surfactant is selected from the group consisting of anionic, cationic, nonionic and amphoteric surfactants and combinations thereof.

8. The composition recited in claim 1 further comprising adjuncts for application to a consumer product selected from the group consisting of granular and liquid laundry detergent, liquid hand dish washing detergents, hair and body shampoos, shave preparation gels, facial cleanser, dentifrices, hard surface cleaners and combinations thereof.

9. The composition recited in claim 8 wherein the adjunct is selected from the group consisting of polymers, builders, enzymes, fragrance, whitening agents, brightening agents, antimicrobial agents and softeners.

10. A consumer product comprising:
    a foam manipulation composition of claim 1; and
    1 to 50% by weight of the composition of surfactant;
    0.02% to 10% by weight of the composition of polymers; and
    from 1-30% by weight of the composition of builders.

11. The consumer product recited in claim 10 wherein the particles are selected from silica and titania.

12. The consumer product recited in claim 10 wherein the surfactant is selected from the group consisting of anionic, cationic, nonionic and amphoteric surfactants and combinations thereof.

13. A consumer product comprising:
    a foam manipulation composition of claim 1.

14. The consumer product recited in claim 13 wherein the ratio of particles-to-surfactant is between about 1:10 to about 10:1.

15. The consumer product recited in claim 13 wherein the contact angle is in the range between about 25° to 140°.

16. The composition recited in claim 13 wherein the particles are solid particles selected from the group consisting of metal oxides, silica, titania, clay, mica, synthetic polymer particles, non woven polymers, starch, cellulose, proteins, and combinations of organic and inorganic particles and combinations thereof.

17. The consumer product recited in claim 13 wherein the surfactant is selected from the group consisting of anionic, cationic, nonionic and amphoteric surfactants and combinations thereof.

18. The consumer product recited in claim 13 wherein the consumer product is selected from the group consisting of granular and liquid laundry detergents, liquid hand dish washing detergents, hair and body shampoos, shave preparation gels, facial cleansers, dentifrices and hard surface cleaners and the product further comprises at least one adjunct.

* * * * *